(12) United States Patent
Kikuyama

(10) Patent No.: US 8,899,743 B2
(45) Date of Patent: Dec. 2, 2014

(54) PROTECTIVE SPRAY PAINTER EYEWEAR

(76) Inventor: Kendall Masao Kikuyama, Aiea, HI (US)

( * ) Notice: Subject to any disclaimer, the term of this patent is extended or adjusted under 35 U.S.C. 154(b) by 19 days.

(21) Appl. No.: 13/199,315

(22) Filed: Aug. 24, 2011

(65) Prior Publication Data

US 2013/0050633 A1   Feb. 28, 2013

(51) Int. Cl.
  *G02C 11/08*   (2006.01)
  *G02C 7/16*   (2006.01)

(52) U.S. Cl.
  CPC . *G02C 11/08* (2013.01); *G02C 7/16* (2013.01)
  USPC .......................................................... 351/62

(58) Field of Classification Search
  USPC ..................... 351/41, 62, 142–144, 158, 200; 2/534–437
  See application file for complete search history.

(56) References Cited

U.S. PATENT DOCUMENTS

| | | | |
|---|---|---|---|
| 1,270,640 A | | 6/1918 | Markham |
| 1,274,257 A | * | 7/1918 | Furlong .............................. 2/433 |
| 1,286,645 A | * | 12/1918 | Jacobs ............................... 2/433 |
| 1,464,883 A | | 8/1923 | Phillips et al. |
| 2,428,411 A | * | 10/1947 | Davis ............................ 384/149 |
| 2,971,196 A | | 2/1961 | Howell |
| 3,231,897 A | | 2/1966 | Woolfolk, Sr. |
| 3,356,439 A | | 12/1967 | Magnus |
| 3,395,406 A | | 8/1968 | Smith |
| 3,867,020 A | | 2/1975 | Braunhut |
| 3,921,223 A | | 11/1975 | Hoyecki |
| 3,922,722 A | | 12/1975 | Pokhodnya et al. |
| 3,944,345 A | | 3/1976 | Decorato |
| 4,011,865 A | | 3/1977 | Morishita |
| 4,126,131 A | * | 11/1978 | Davis et al. .............. 128/201.15 |
| 5,718,500 A | | 2/1998 | Vinci guerra et al. |
| D571,847 S | | 6/2008 | Campbell et al. |
| 2005/0114986 A1 | | 6/2005 | Hobart |
| 2007/0252946 A1 | * | 11/2007 | Welchel et al. .................. 351/62 |
| 2010/0146685 A1 | | 6/2010 | Carter |

FOREIGN PATENT DOCUMENTS

| FR | 372473 | 2/1907 |
|---|---|---|
| GB | 540267 | 10/1941 |

OTHER PUBLICATIONS

Hsia-Ting Chang, The Slanties: Rad or ridiculous new eyewear?, The John Hopkins News-Letter, www.jhunesletter.com, posted on Apr. 23, 2009.
Tim Hill, Critic's Pick, Baltimore City Paper, Apr. 15, 2009.
1960's Chop Suey Specs, eBaum's World.

(Continued)

*Primary Examiner* — Scott J Sugarman
*Assistant Examiner* — Robert E Tallman
(74) *Attorney, Agent, or Firm* — Martin E. Hsia

(57) ABSTRACT

A frame with an outer lens having a slit that stagnantly sealingly conforms to the user's face to create a stagnant air barrier that creates air resistance against airborne particles entering the slit, traversing the interior space, and then contacting the user's eyes. The user can see through the slit even if airborne particles deposited on the outer lens obscure the user's vision. Alternatively, a frame with an outer lens having slits for a user's eyes and a protective inner lens having transparent portions has an inlet communicating with the interior space created between the inner and outer lenses. A portable compressed air source introduces compressed air into the interior space to create an air stream that flows outwardly through the slits. The air stream prevents airborne particles from entering through the slits and into the interior space and contacting the inner lens, to maintain transparency. The user can carry the compressed air source and move freely.

12 Claims, 19 Drawing Sheets

(56) References Cited

OTHER PUBLICATIONS

Bill Ryan and Scott Shin, "Safety from Head to Toe," American Painting Contractor, Jul. 2010, vol. 87, No. 6, p. 20.
IDBarn.com, Narrow Frame Sunglasses, at http://www.idbarn.com/index.php?action=results&kw=narrow+frame+sunglasses.
The Honey Room, Black Space Age Futuristic Sunglasses, at http://www.thehoneyroom.com/pd-black-space-age-futuristic0sunglasses.cfm.
Eyeglasses Warehouse, Space Age, Machine Age, Art Deco, Custom Made Safelight Sunglasses, at http://www.eyeflasseswarehouse.com/pages/3102-04.html.
CoatingsPro Magazine, Bolle enters U.S. Safety Eyewear Market, May 2011, p. 67.
Wikipedia Article, Inuit Snow Gogggles http://en.wikipedia.org/wiki/Inuit_snow_goggles.
http://www.jefpat.org/images/CuratorsChoiceImages/Year%202013/Dec2013/inuit%20goggles-edited.jpg.
http://25.media.tumblr.com/tumblr_lyv7yoHGtr1qzigwwo1_400.jpg.
http://rlv.zcache.com/inuit_sun_snow_glasses_posters-r6ccf447747b545289afafe015aa717fe_wvy_8byvr_512.jpg.
Cunningham, Kevin and Peter Benoit. The Inuit. Scholastic, Children's Press, A True Book, 2011, p. 23.
Ipellie, Alootook with David MacDonald. The Inuit Thought of It: Amazing Arctic Innovations. Annick Press Ltd., 2007, 4th printing, Apr. 2012, p. 27.

\* cited by examiner

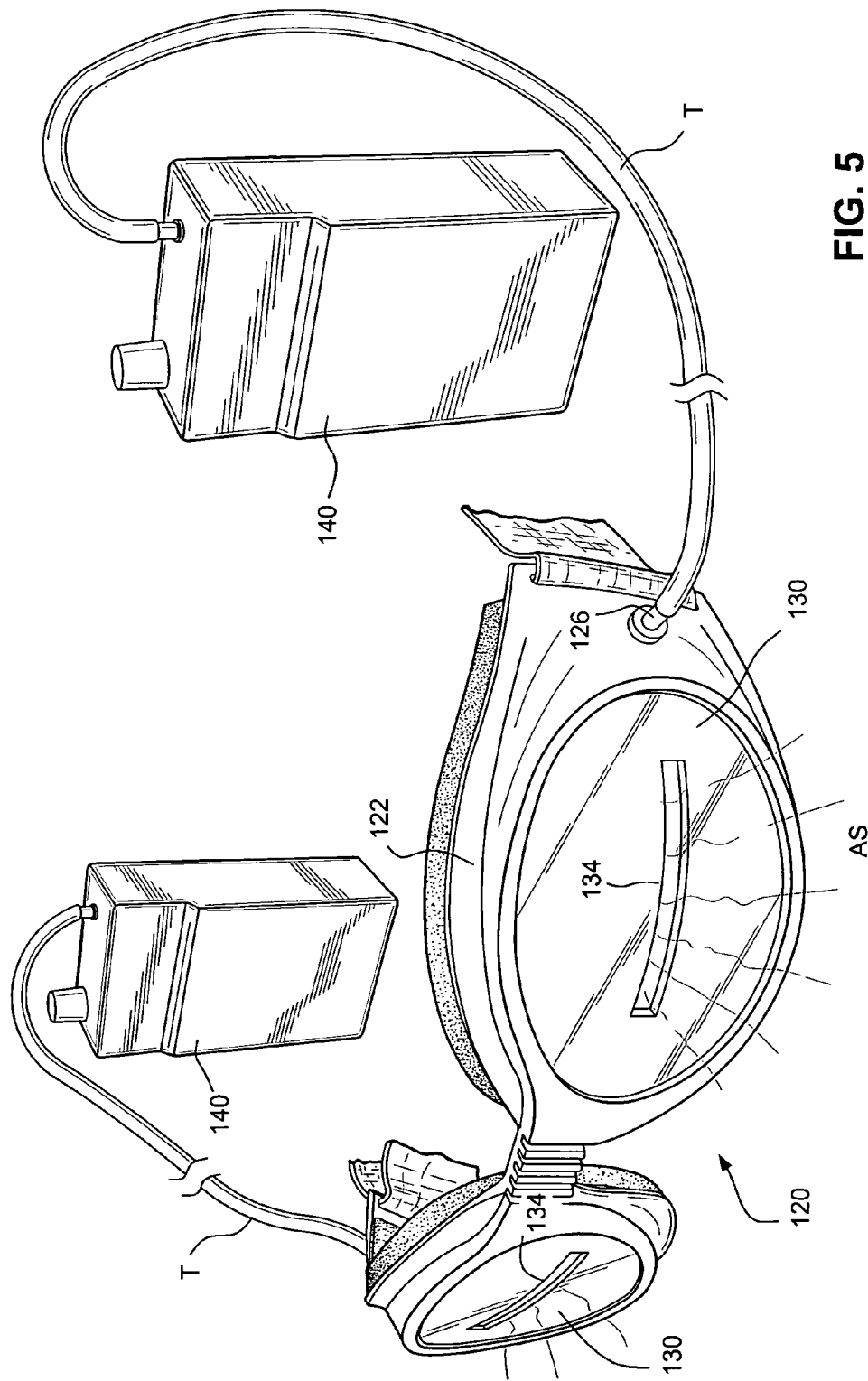

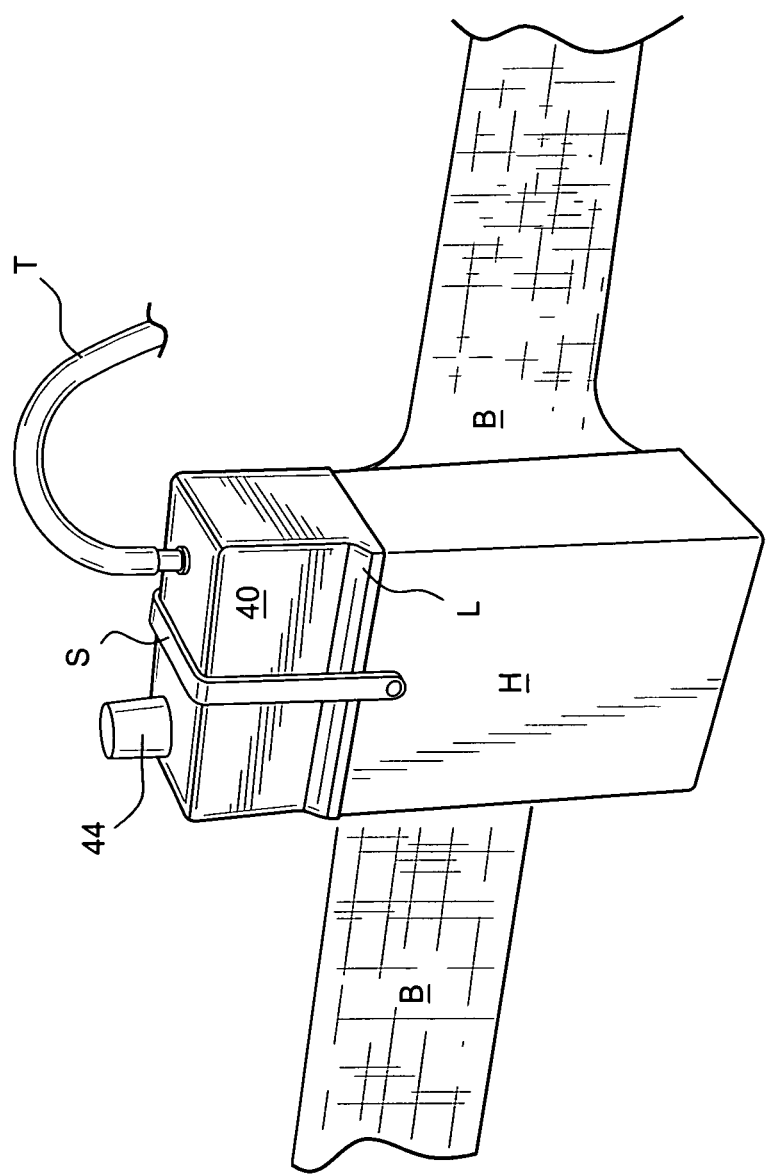

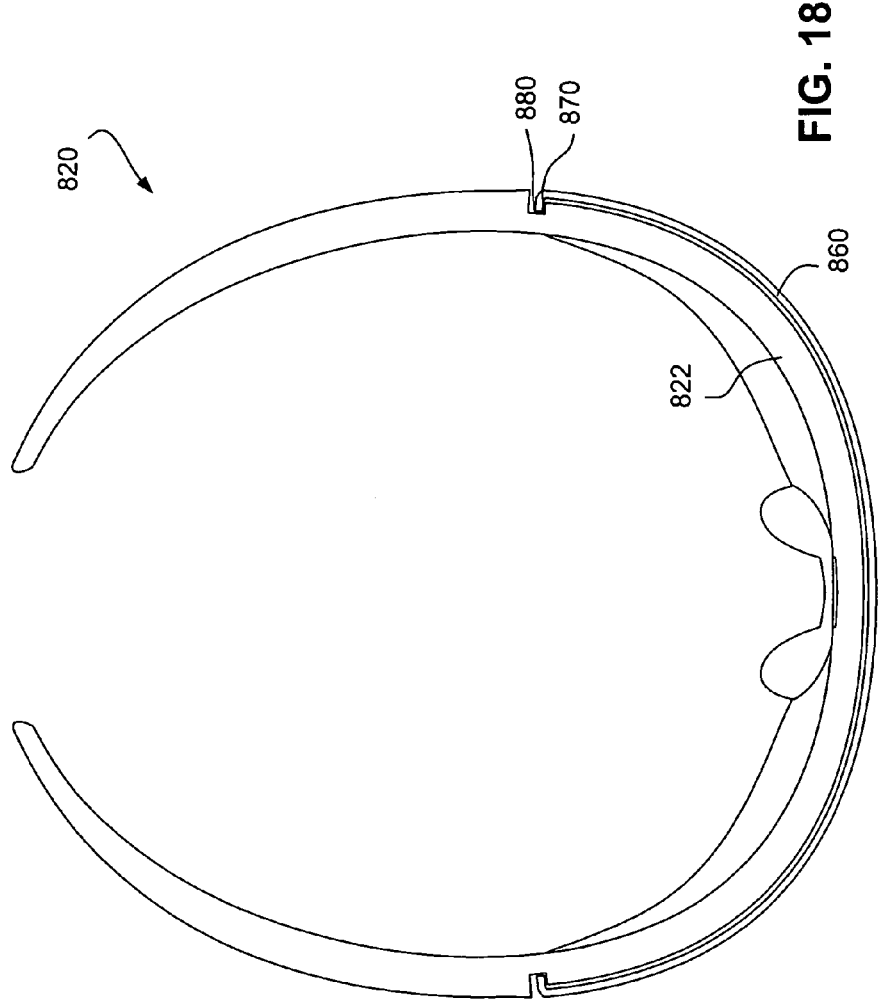

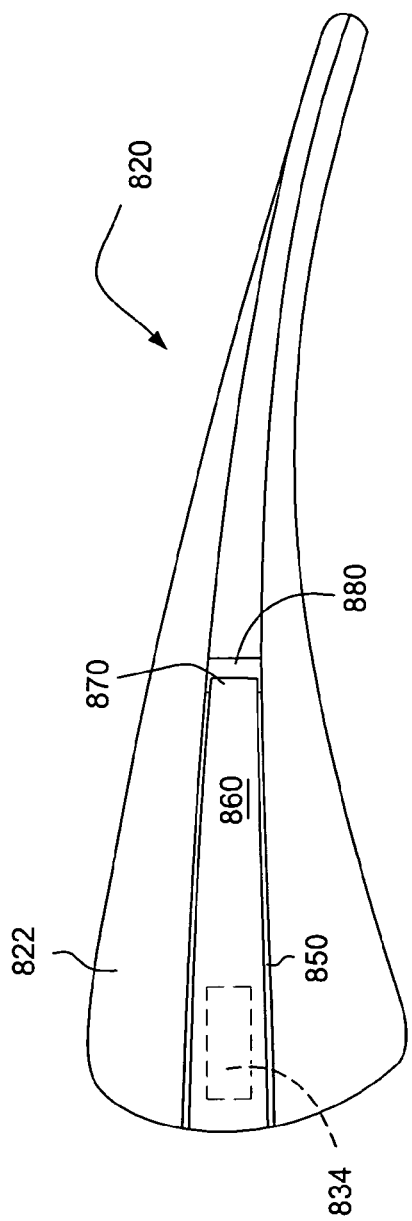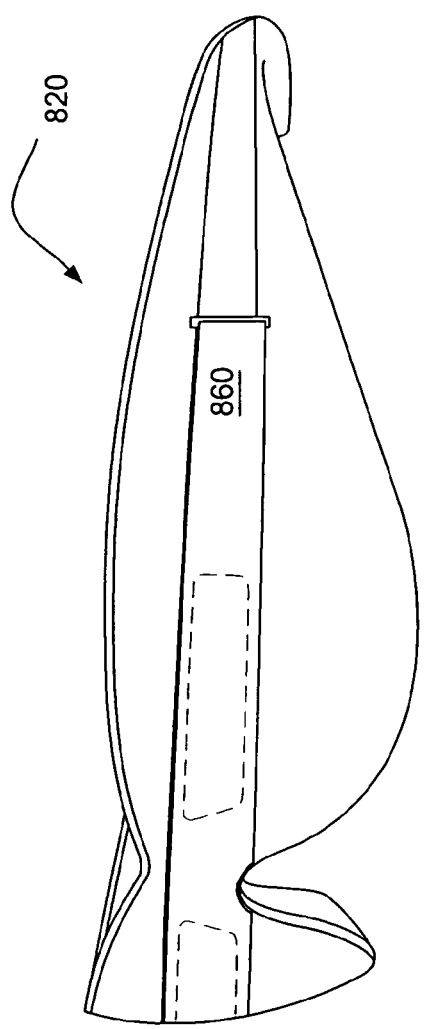

PROTECTIVE SPRAY PAINTER EYEWEAR

TECHNICAL FIELD

This invention relates to eyewear that simultaneously protects a user's eyes from airborne particles and avoids the accumulation of airborne particles on such eyewear that would obscure the user's vision. More specifically, this invention relates to protective eyewear that can be used by spray painters, optionally with a portable compressed air source, so that the painters can continue working and move freely, despite the presence of airborne paint particles. However, this invention can be used in any situation in which it is desired to protect a user's eyes, and enable the user to continue working, despite the presence of airborne particles whose accumulation on the eyewear may obscure vision, such as dust or pollen.

The user of a spray painting device is exposed to airborne paint particles, called "overspray", while using the device. The paint particles float in the air and can come into contact with the user's eyes. Although the user can use protective eyewear to protect his or her eyes, such as goggles, glasses or a visor, paint particles will soon accumulate on the eyewear and obscure the user's vision, so that the user must then stop working to clean or replace the lenses in the eyewear. Because of these difficulties, users often decide to perform spray painting without any protective eyewear at all. However, for worker safety, protective eyewear should be worn by the users to protect against debris and other hazards (in addition to airborne particles), and protective eyewear may also be mandated by safety regulations. Moreover, in certain types of painting applications, the airborne paint particles can be very harmful to the user's eyes, especially if the paint is toxic, based on non-water-soluble solvents, or otherwise harmful, or if the painting is being done in an enclosed environment, so that the concentration of airborne particles is greatly increased while painting.

There have been many suggested solutions to the problem of providing protective eyewear for spray painters, but none has been satisfactory. For example, many devices have been provided that blow jets of air across or against the front of protective eyewear to blow airborne paint particles away. However, air being blown across or against the front of the eyewear may diffuse and render the device ineffective, and may mix with the airborne particles and create turbulent air currents and eddies to bring them into contact with the eyewear. Further, some of these devices require connection to a fixed source of compressed air, so that the user cannot move freely.

It is therefore an object of this invention to provide protective eyewear that will avoid the accumulation of paint particles that obscures a user's vision, thereby causing the user to stop work until the eyewear can be cleaned or replaced.

It is a still further object of the present invention to provide such a device that allows the user to move freely.

It is a still further object of the present invention to provide such eyewear that is simple and inexpensive to construct.

BACKGROUND ART

Eyewear named "Slanties" comprising a solid flat wooden mask, shaped like oversized sunglasses, with slits for the eyes, was sold in the United States in 2009. However, these "Slanties" were flat, and therefore did not conform to the user's face in any manner.

U.S. Pat. No. 5,718,500 to Vinci Guerra, et al. discloses an impact resistant positive pressure lens consisting of a first lens integrally formed with an air inlet chamber to effect an air flow through and out a second lens that is provided with air nozzles. The air nozzles direct the flow of air forward of the second lens to prevent paint overspray from adhering to the second lens.

U.S. Pat. No. 4,011,865 to Morishita discloses a face covering dust-proof protection mask having small air blowers feeding air under pressure into a face covering type mask. A viewing window is provided on the front surface of the mask body and a transparent guard glass with suitable clearances for allowing blowing-off of air therearound are oppositely fitted inside a viewing window. In addition, numerous small clearances are formed circumferentially between the inner side peripheral edge of the mask body and the face of a user to provide for air leak-off.

U.S. Pat. No. 3,231,897 to Woolfolk, Sr. discloses a goggle construction providing a protective curtain of air about the vision openings in the goggles to prevent dust particles and the like from entering the vision openings of the goggles without using transparent lenses for the purpose. A plurality of individual air outlets are provided to form curtains of air about the vision openings. However, these individual air outlets are circumferentially formed in the frame so that they may be dissipated or diffused and thereby lose effectiveness. Further, there is no disclosure of whether the source of compressed air is portable or not.

U.S. patent application Ser. No. 10/724,230 (Publication No. US 2005/0114986 A1), now abandoned, by Hobart, discloses a painter's mask having a header with a number of spaced atomizers to deliver jets of pressurized air over and in front of the shield.

U.S. Pat. No. 1,464,883 to Phillips et al. discloses a painter's mask having annular conduits surrounding eye pieces with discharge apertures distributed thereabout, so that currents of air encircling the glass meet at a point a short distance in front of the surface of the glass.

U.S. Pat. No. 3,922,722 to Pokhodnya et al. discloses a protective housing having a perforated pipe located on the outside used to divert aerosol flow using air coming out of the perforations.

U.S. Pat. No. 3,921,223 to Hoyecki discloses an air shield for welders comprising a hollow tube perforated along its length and contoured to encircle the neck with openings arranged to direct jets of air outwardly to form an air shield or curtain which disperses fumes and protects the operator.

U.S. Pat. No. 2,971,196 to Howell discloses goggles with an attached washing means so that liquid delivered through a member on the goggles flushes the outer surfaces.

DISCLOSURE OF INVENTION

The above and other objects are achieved by a device comprising, in a single simple lens passive embodiment (where "simple lens" refers to a single lens, and "passive" refers to lack of compressed air), a frame configured to wear over a user's eyes and an outer lens retained in the frame having a slit for the user's eyes through which the user can see. The improvement comprises configuring the frame to place the lens in front of the user's eyes and to stagnantly sealingly conform to the user's face, to create a stagnantly sealed interior space in front of the user's eyes. Air in the interior space becomes a stagnant air barrier that creates air resistance against airborne particles entering the slit, traversing the interior space, and then contacting the user's eyes. In this manner, the user can see through the slit even if airborne particles deposited on the outer lens obscure the user's vision.

The frame preferably stagnantly sealingly conforms to the user's face either by being shaped to stagnantly conform, or having an attached sealing gasket. Stagnantly sealed or stagnantly sealingly conform includes fully sealed, and means sealing at least sufficient that air in the stagnantly sealed space becomes stagnant, calm, or "dead", and therefore creates air resistance against airborne particles entering the slit, traversing across the interior space, and contacting the user's eyes, just as streams of particles carried by fluids encounter resistance from any stagnant medium through which they may travel so that they stop.

Because the interior space is stagnantly sealed, the air in the interior space forms a "pocket" of stagnant air, or "dead air", thus providing a stagnant air barrier that substantially protects the user's eyes from the airborne particles. Indeed, the "pocket" of "dead" air is heated by the user's body heat and expands outwardly somewhat to further resist the intrusion of air and airborne particles through the slits.

Optionally, in a compound lens embodiment, an inner lens (without a slit), transparent in the portions between the user's eyes and the slit in the outer lens, can be interposed between the outer lens and the user's eyes, to protect the user's eyes more completely.

Optionally also, the frame and lens with slit can be integrally formed, so there would be no separate frame, lens aperture in the frame, or lens.

In a two simple lens passive embodiment, with one lens for each eye, the device comprises a frame configured to wear over the user's eyes that stagnantly sealingly conforms to the user's face, either by being shaped to conform, or having an attached sealing gasket.

A pair of lenses, each having a slit for one of the user's eyes, is preferably removably, and stagnantly sealingly, retained by each of the lens retainers, so that the user can see through the slits. As above, this forms a stagnantly sealed interior space between the lenses and the user's face. Because the interior space is stagnantly sealed, the air in the interior space forms a "pocket" of "dead air", that is, a stagnant air barrier, to provide resistance against airborne particles entering the slits and traversing the interior space into the user's eyes, thus substantially protecting the user's eyes from the airborne particles.

Indeed, as above, the "pocket" of "dead" air is heated by the user's body heat and expands outwardly somewhat to further resist the intrusion of air and airborne particles through the slits. Optionally, a pair of removable inner lenses, transparent in part, can be provided to protect the user's eyes more completely. Optionally also, the frame and lens with slits can be integrally formed.

In a single compound lens active embodiment (where "compound lens" means separate inner and outer lenses, and "active" means using a compressed air source), a frame configured to wear over a user's eyes is provided, and a preferably removable outer lens having a slit for each of the user's eyes is retained in the frame so that the user can see through the slits. A preferably removable protective inner lens that is transparent at least in the portions between the user's eyes and the slits is retained behind the outer lens so that the user can see through both the transparent portions of the inner lens and through the slits. A partially sealed "inter-lens" space is thereby created between the inner lens and the outer lens. An inlet is provided through the frame that is in fluid communication with the inter-lens space. Preferably, with this construction, when a compressed air source pumps air through an air tube connected to the inlet into the inter-lens space, positive air pressure is created in the inter-lens space and an air stream flows outwardly through the slits. By partially sealed is meant that the inter-lens space can be completely sealed, but is at least sufficiently sealed that when the compressed air is pumped through the inlet into the inter-lens space, an air stream flows outwardly through the slits. The air stream prevents airborne particles from entering the inter-lens space and contacting the inner lens, so that transparency of the transparent portions of the inner lens is maintained. Thus, the user can see through the inner lens and the slits in the outer lens, despite any accumulation of airborne particles on the outer lens. The single lens construction also allows this embodiment to be used by people who normally wear eyeglasses, because the bridge (nosepiece) between the two lenses of the eyeglasses can be accommodated within the interior space between the user's face and the inner lens, which would not be the case with embodiments having two separate lenses, as described below. Preferably, the compressed air source is a portable compressed air source, so that the user can carry the compressed air source and move freely.

In a two compound lens active embodiment, the device comprises a frame configured to wear over the user's eyes. A pair of preferably removable outer lenses, each having a slit for one of the user's eyes, is retained in the frame, so that the user can see through the slits. A pair of preferably removable inner lenses that are transparent in the portions between the user's eyes and the slits is also retained in the frame so that the user can see through both the transparent portions of the inner lenses and through the slits. This forms an inter-lens space between each inner lens and outer lens. Inlets extend through the frame in fluid communication with the inter-lens space between each inner lens and outer lens. When a compressed air source is connected via an air tube to an inlet, positive air pressure is created in the inter-lens space and an air stream flows outwardly through the slit, which prevents airborne particles from entering the inter-lens space and contacting the inner lens, thus maintaining transparency of the transparent portions. Again, preferably the user can carry the compressed air source and move freely.

Preferably the compressed air source is either a portable cordlessly powered pump or a compressed gas canister. Preferably also, the retainers are grooves, ridges or tabs formed in, or attached to, the frame. Preferably also, the outer lens is transparent.

In still another embodiment, the invention comprises the process of using a frame configured to wear over a user's eyes having slits for each of a user's eyes, whereby said user's vertical field of view is at most approximately 90 degrees, to substantially reduce amounts of nontoxic airborne particles contacting the user's eyes because substantial amounts of nontoxic airborne paint particles contact the frame or the user's face. Thus, the user avoids stopping work to remove paint particles that obscure vision.

BRIEF DESCRIPTION OF DRAWINGS

FIG. 5 is a front perspective view of a second embodiment of the present invention with an air pump for each side of protective eyewear having a pair of lens apertures and an alternative rectangular configuration of slits.

FIG. 6 is a perspective front view of a holster on a belt for holding one of the air pumps of FIG. 5.

FIG. 18 is a top plan view of the embodiment of FIG. 16 with the optional sunglass portion of FIG. 17 snapped in.

FIG. 19 is a side elevational view from the left of the embodiment of FIG. 16, the side elevational view from the right being a mirror image thereof.

FIG. 20 is a side elevational view diagonally from the front left of the embodiment of FIG. 16 with the optional sunglass portion of FIG. 17 snapped in.

BEST MODES FOR CARRYING OUT INVENTION

The presently preferred best modes for carrying out the present invention are illustrated by way of example in FIGS. 1-23.

Figure 1:
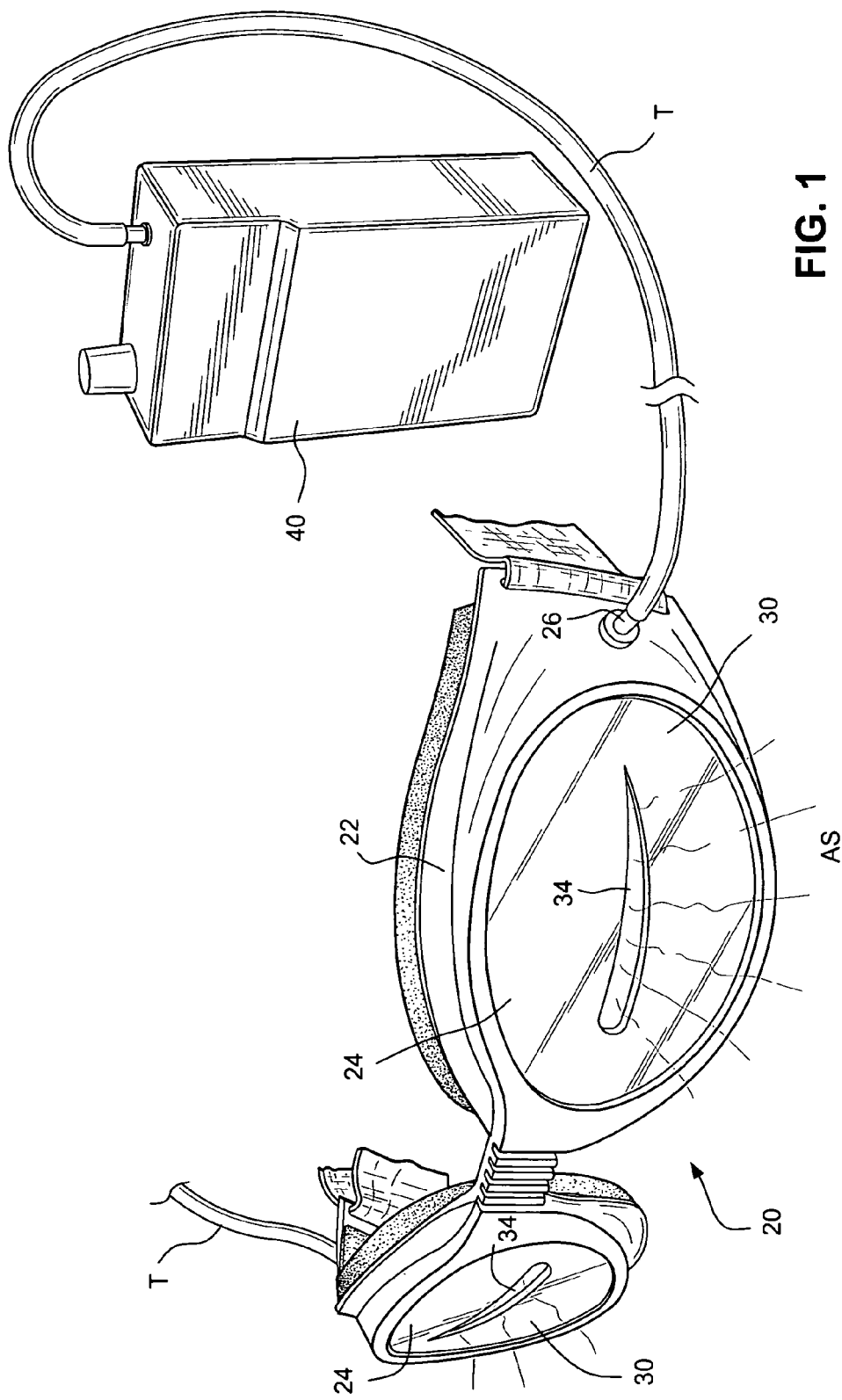
FIG. 1 is a front perspective view of a device according to the present invention, with a single pump providing air to a pair of air inlets on protective eyewear having a pair of lens apertures with teardrop shaped slits.

Referring to FIG. 1, shown is a first presently preferred embodiment of protective eyewear 20 according to the present invention, in which a frame 22 configured to wear over a user's eyes has a pair of lens apertures 24.

Figure 4:
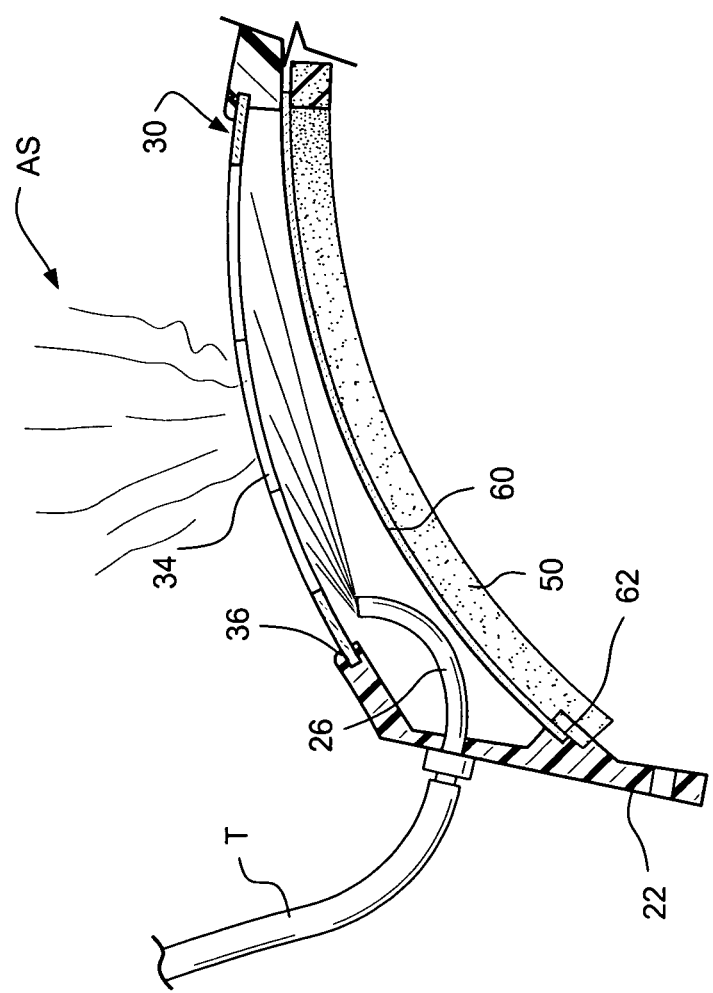
FIG. 4 is a top cross sectional view of one side of the eyewear of FIG. 1.

A pair of preferably removable outer lenses 30, each having a preferably teardrop shaped slit 34 is stagnantly sealingly retained in the lens apertures by peripheral outer lens retainers (See FIG. 4). Although the slit is preferably rectangular or teardrop shaped, the slit in this and all other embodiments can be any shape through which the user can see, as long as the slit is small enough to reduce or prevent intrusion by airborne particles. For example, the slit can be square, round, almond shaped, semicircular, diamond shaped, or any other shape. Preferably the outer lenses 30 are transparent (in all embodiments), so that the user can have a greater field of view than through the slits 34. If that greater field of view is obscured by accumulation of paint particles or other visual obstructions on the lenses 30, the user can restore the greater field of view at any desired time by wiping them away. An inlet 26 is provided in the frame 22. An air tube T connects the inlet 26 to a compressed air source (here a portable cordlessly powered pump) 40.

Figure 2:
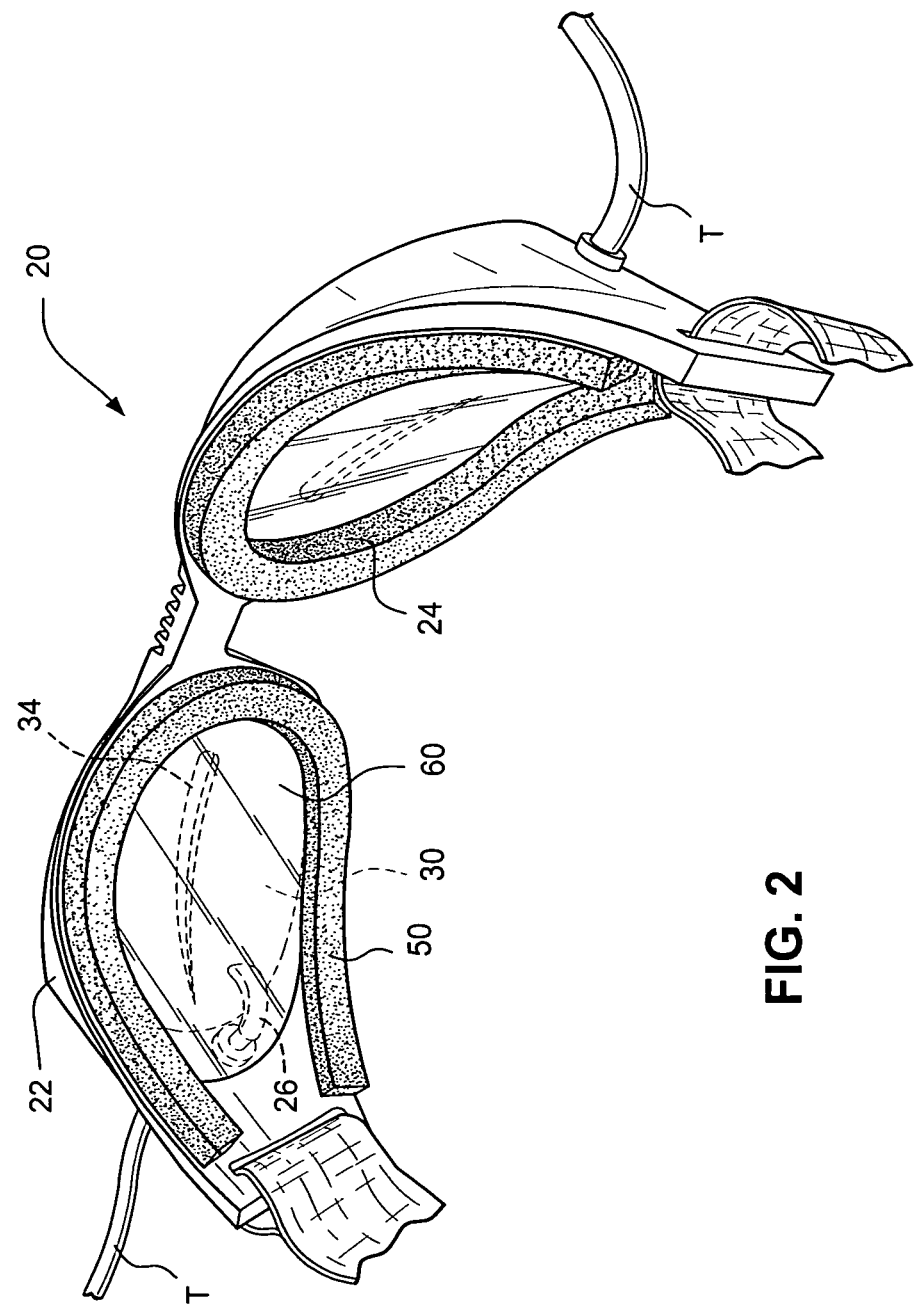
FIG. 2 is a rear view of the protective eyewear of FIG. 1.

Referring to FIG. 2, shown is a rear view of the protective eyewear 20 of FIG. 1. An optional sealing gasket 50 is provided between the frame 22 and the user's face, to prevent airborne particles from contacting the user's eyes when wearing the eyewear 20.

As can be seen, the inlet 26 extends through the frame 22.

Figure 3:
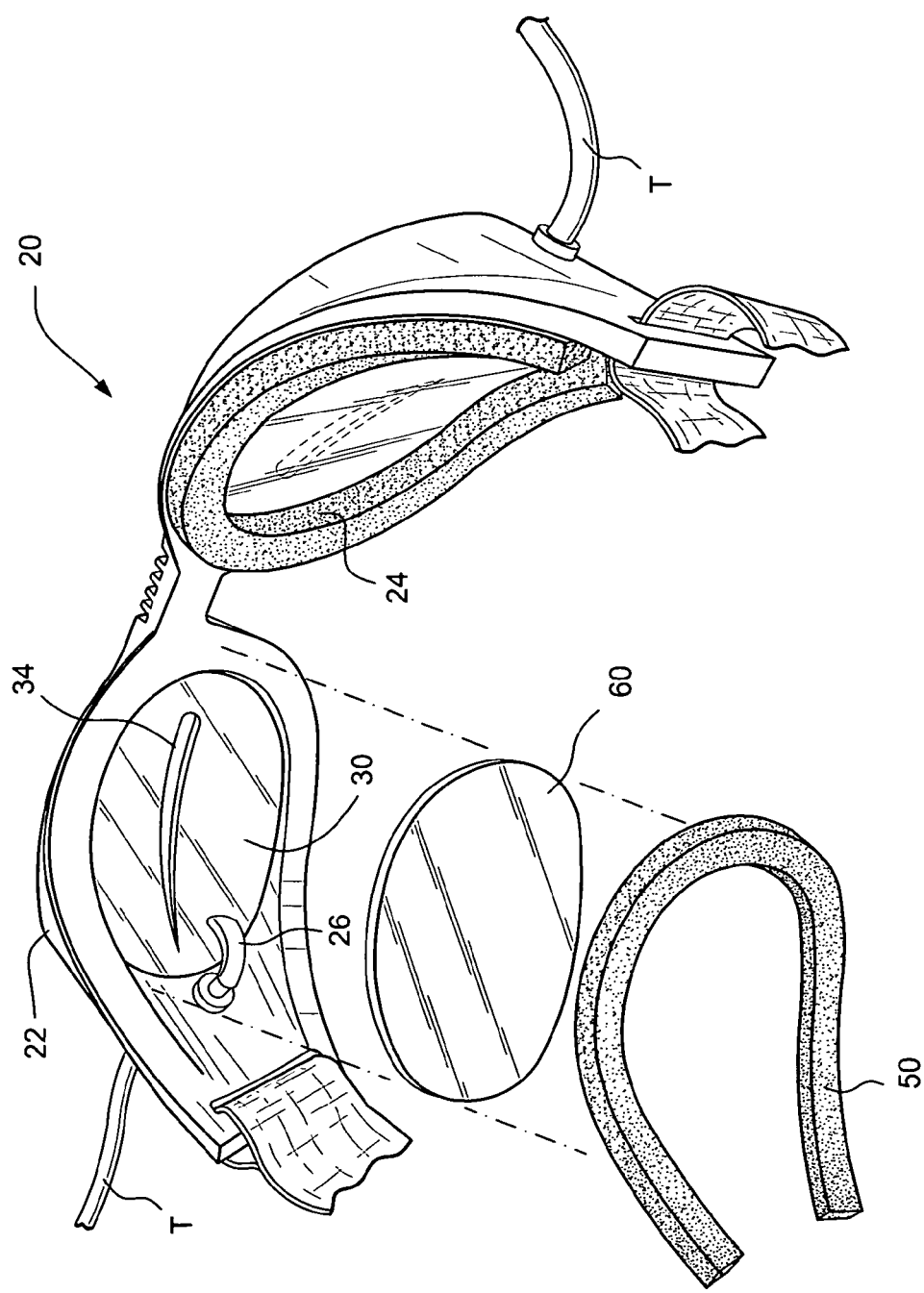
FIG. 3 is an exploded rear view of the eyewear of FIG. 1.

Referring to FIG. 3, shown is an exploded rear view of one side of the eyewear 20 of FIG. 1. As can be seen, the preferably removable outer lens 30 having slit 34 is retained in the lens aperture 24, and inlet 26 provides fluid communication from the tube T into the inter-lens space created between the outer lens 30 and an inner lens 60. Preferably the inner lens is transparent at least in the portions between the user's eyes and the slits 34, so that the user can see through the inner lens 60 and out the slits 34.

Referring to FIG. 4, shown is a top cutaway view of the eyewear of FIG. 3, showing that the inlet 26 is in fluid communication with an inter-lens space created between the inner lens 60 and the outer lens 30. As can be seen, the preferably removable outer lens 30 is retained in position by fitting into retainer groove 36, and the preferably removable inner lens 60 is retained in position by a retainer groove 62. The inner lens 60 and the outer lens 30 are preferably removable for cleaning or replacement, and are also preferably retained by the retainers to form a partially sealed inter-lens space. The inter-lens space is preferably positive pressure sealed (as described below) so that air pumped through the tube T to the inlet 26 creates positive air pressure in the inter-lens space so that air flows outwardly through the slit 34 in order to prevent airborne particles from entering the inter-lens space through the slit 34 and contacting the inner lens 60, so as to maintain transparency of the inner lens 60.

It is preferred that the inlet 26 points towards the outer lens 30 and slit 34 so that the air from the inlet 26 is directed away from the user's eyes, to avoid drying the user's eyes. It must be noted that the inlet 26 preferably does not send air in a strong stream directed out the slit 34, but preferably only provides enough air to create positive pressure in the inter-lens space to cause an air stream AS that is strong enough to prevent airborne particles from entering the inter-lens space.

By stagnantly sealingly retained or stagnantly sealingly conform or stagnantly sealingly sealed is meant that the retainers or the frame do not need to form an airtight seal, but need only provide a sufficient seal that air retained in an interior space becomes stagnant or "dead" air, as described above. To stagnantly sealingly conform to (or form a stagnant seal with) a user's face also includes (without limitation) (a) to stagnantly sealingly conform only to those portions of the user's face surrounding the eyes, where the temples, forehead, cheeks, eyebrows and nose shall be considered to be a portion of the user's face surrounding the eyes; and (b) for embodiments with compound lenses, to conform sufficiently to the user's face to prevent substantial amounts of airborne particles from passing between the frame and the user's face and thereby contacting the user's eyes, even if no seal is formed, such as with cloth or bristles or other non-sealing contact between the frame and the user's face. The slits 34 are preferably at least large enough for the user to be able to see the work that needs to be performed, but small enough that air pumped through the tube T into the interior space creates sufficient positive air pressure to create the air stream AS to prevent entry of airborne particles into the space. The enclosure of the inner lens 60 by the outer lens 30 to form the inter-lens space causes the air pumped through the inlet 26 to create a positive pressure and the air stream AS flowing outwardly from the slits 34—without the outer lens, air pumped through the inlet 26 would only blow across the inner lens and be dissipated. The vertical field of view provided by the slit only needs to be large enough for the user to perform his or her work. A practical vertical field of view is between approximately 90 degrees and approximately 10 degrees; a preferred vertical field of view is between approximately 60 degrees and approximately 30 degrees; and an optimal vertical field of view is between approximately 45 degrees and approximately 40 degrees.

Referring to FIG. 5, shown is an alternative embodiment 120 with a frame 122, an outer lens 130 and a rectangular configuration of slits 134. Also, two air tubes T are provided, with each connected to a separate pump 140 at one end and an inlet 126 at the other.

Referring to FIG. 6, shown is a close-up view of a presently preferred embodiment of a compressed air source 40 of the present invention, preferably comprising a battery powered pump having a control knob 44 to control the rate of air flow. Preferably the pump 40 can be retained in a holster H on a belt B that can be worn by the user. Optionally, the pump 40 can also be retained in the holster H by a strap S. Optionally, a lip L is provided on the pump 40 to prevent the pump 40 from passing through the holster, because it is preferred that the holster H does not have a bottom.

Figure 7:
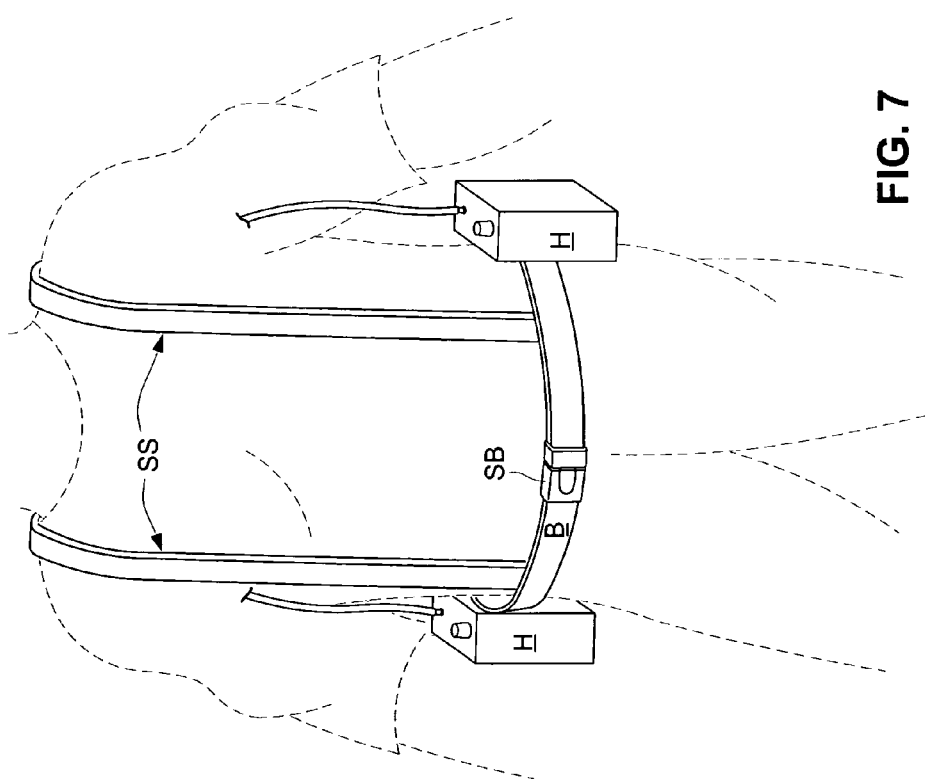
FIG. 7 is a front view of two holsters according to FIG. 6 with optional supplemental shoulder straps.

Referring to FIG. 7, shown are two holsters H according to FIG. 6, with shoulder straps SS to be worn by the user, with an optional snap buckle SB for retaining the belt B.

Figure 8:
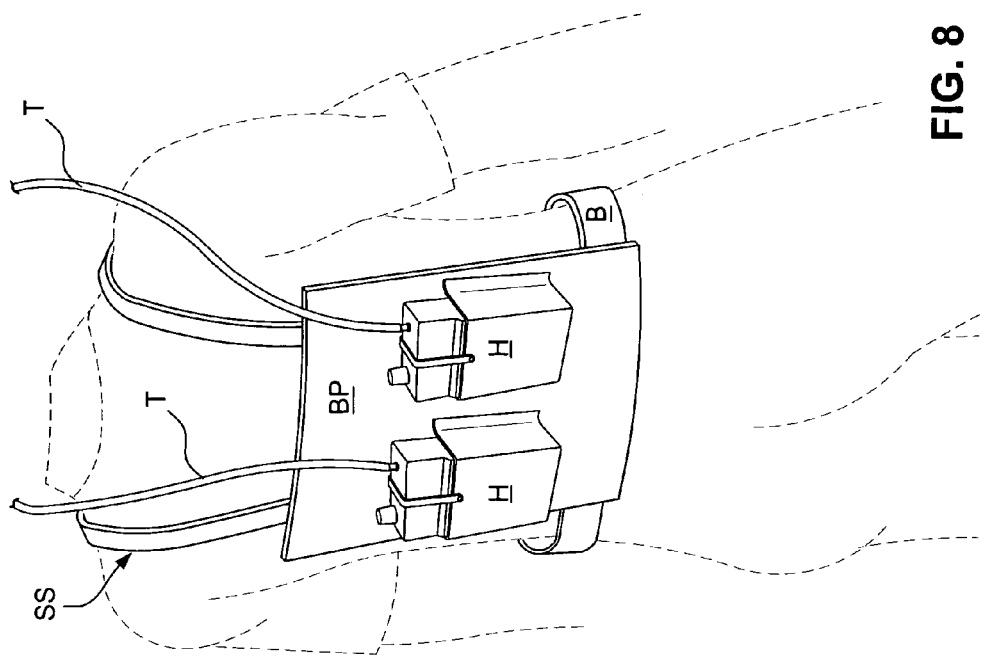
FIG. 8 is a rear view of an alternative embodiment of the present invention in which two air pumps are held in a backpack that is retained on the user through belt straps and shoulder straps.

Referring to FIG. 8, shown is an alternative embodiment in which the holsters H are retained on the back of the user by a backpack BP that is held by the belt B.

Figure 9:
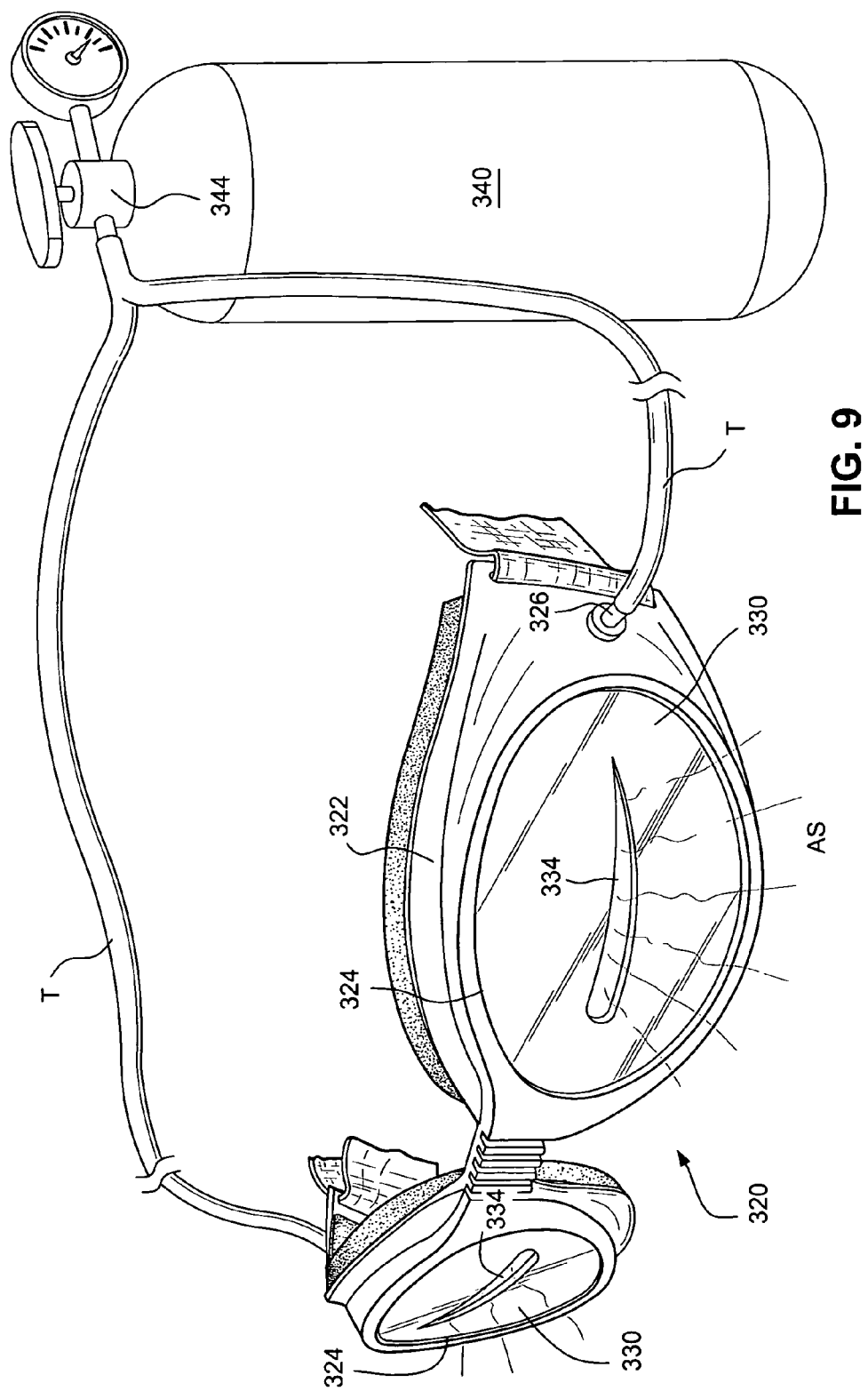
FIG. 9 is a front view of another alternative embodiment of the present invention in which a single compressed air tank provides air for a pair of air hoses connected to eyewear having a pair of lens apertures.

Referring to FIG. 9, shown is another alternative embodiment of the present invention comprising eyewear 320 having a frame 322 with two lens apertures 324. As with the other embodiments described above, preferably removable outer lenses 330 having slits 334 are retained in lens apertures 324, and air tubes T are connected to inlets 326. In this embodiment, the compressed air source 340 is a compressed air bottle with a regulator 344 to control the rate of air flow.

Figure 10:
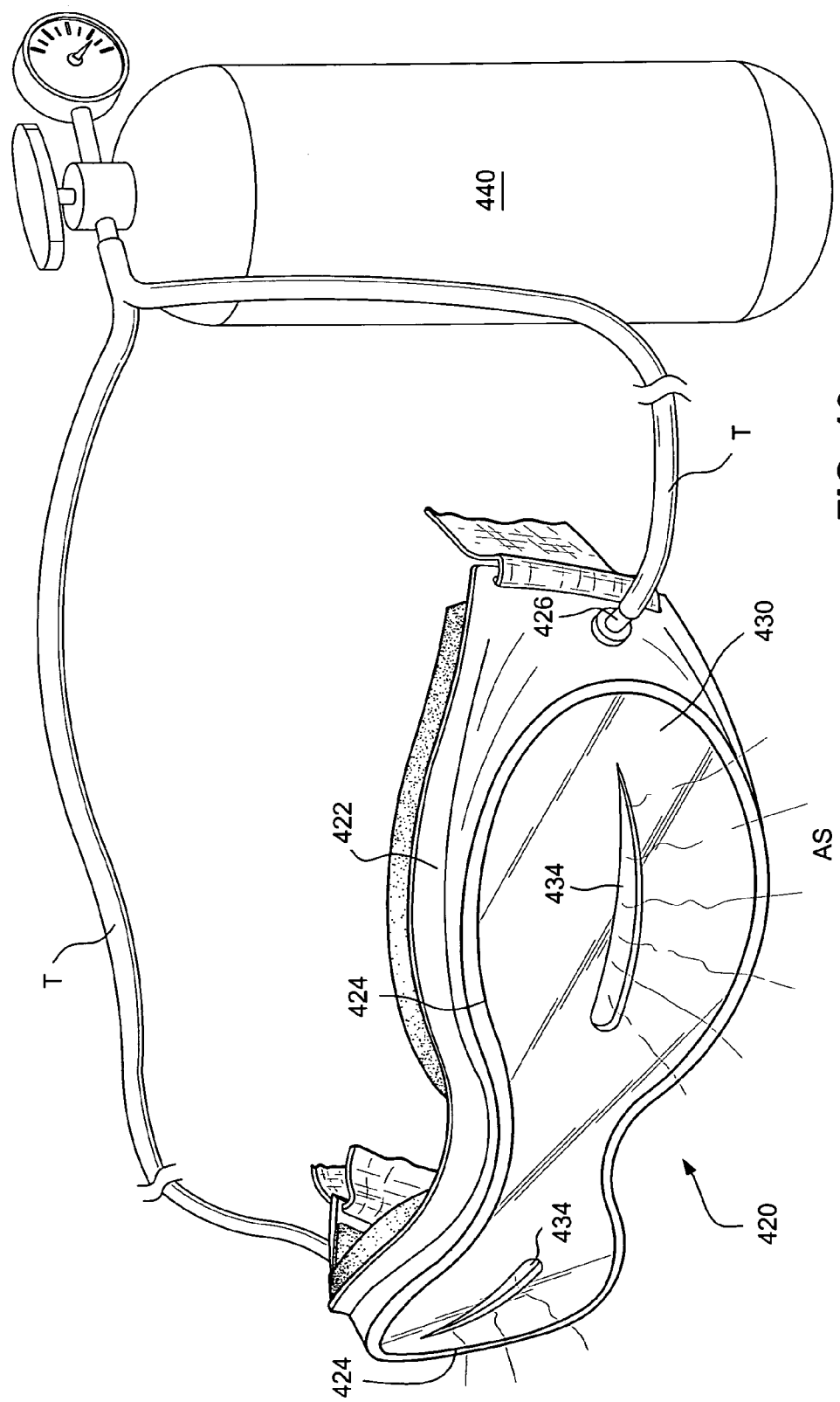
FIG. 10 is a front view of still another alternative embodiment of the present invention in which a single compressed air tank provides air through a single air line to protective eyewear having a single lens aperture with two teardrop shaped slits for a user's eyes.

Referring to FIG. 10, shown is another alternative embodiment comprising eyewear 420 having a frame 422 with a single lens aperture 424 in which a single preferably removable outer lens 430 having two slits 434 is retained in the lens aperture 424. Because there is only a single outer lens 430 and a single inner lens (not shown), only a single inlet 426 is necessary. In this embodiment, the compressed air source is a compressed air tank.

As can be seen from the foregoing description, in operation, the slits 434 in the outer lens 430 are maintained free of airborne particles by the air stream AS and therefore the user can see through the slits at all times. It is preferred that the inner lens (not shown) also be provided because occupational safety regulations require that workers' eyes be protected.

The prior art does not disclose or suggest a partially sealed inter-lens space created between inner and outer lenses in which an air stream flows directly outwardly through slits in the outer lenses in order to prevent airborne particles from contacting the transparent inner lens, thereby maintaining transparency of the inner lens and the user's ability to see through the slits while spray painting. The prior art primarily relates to blowing air across a single lens, or forwardly from the periphery of a lens. Further, the prior art does not disclose or suggest the use of a portable compressed air source in combination with such eyewear so that the user can move freely.

Figure 11:
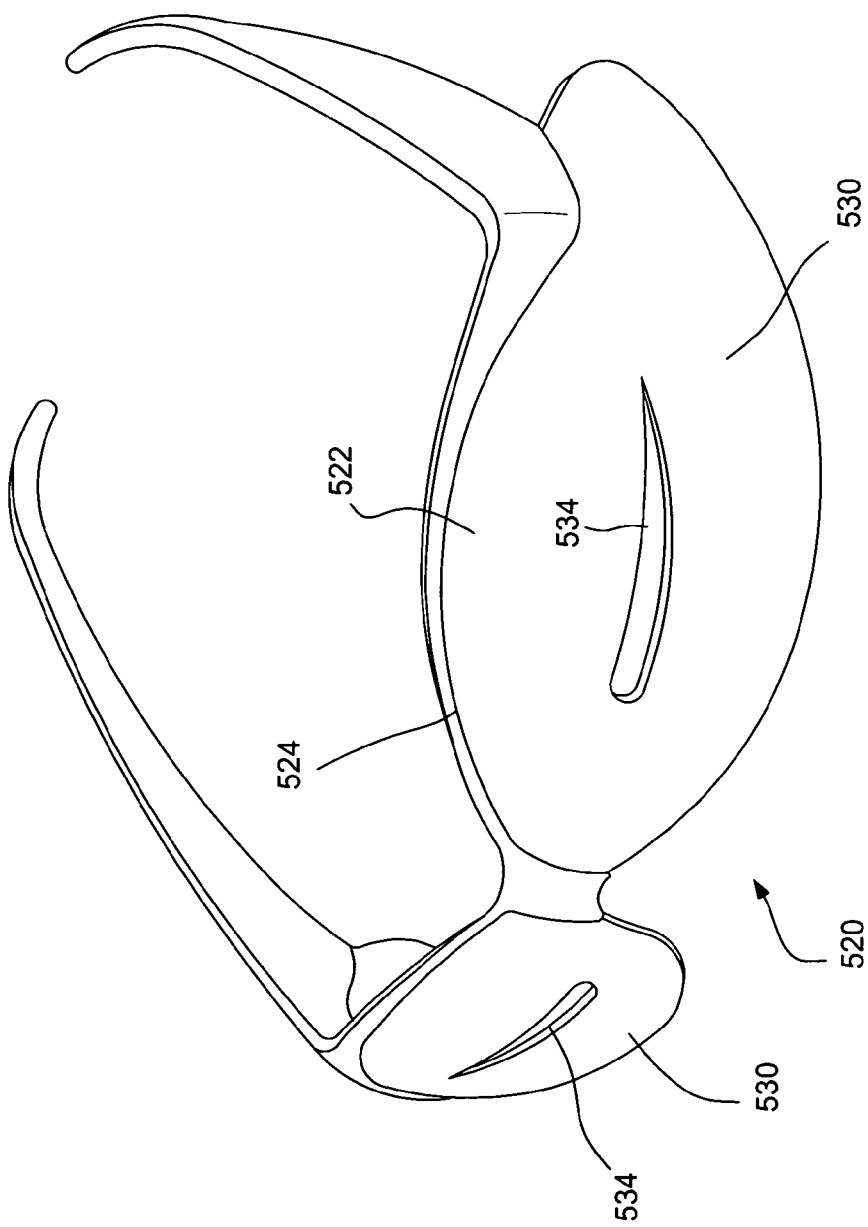
FIG. 11 is a front perspective view of still another alternative embodiment of the present invention with two lens apertures, but that does not have air inlets or a compressed air supply.

Referring to FIG. 11, shown is still another alternative embodiment comprising eyewear 520 having a frame 522 shaped to stagnantly sealingly conform to the user's face that has a pair of lens apertures 524. A pair of preferably removable outer lenses 530, each having a slit 534, is retained in the lens apertures by lens retainers (see FIG. 4) in front of the user's eyes.

Preferably, this embodiment only contains outer lenses, but inner lenses can optionally be provided.

Figure 12:
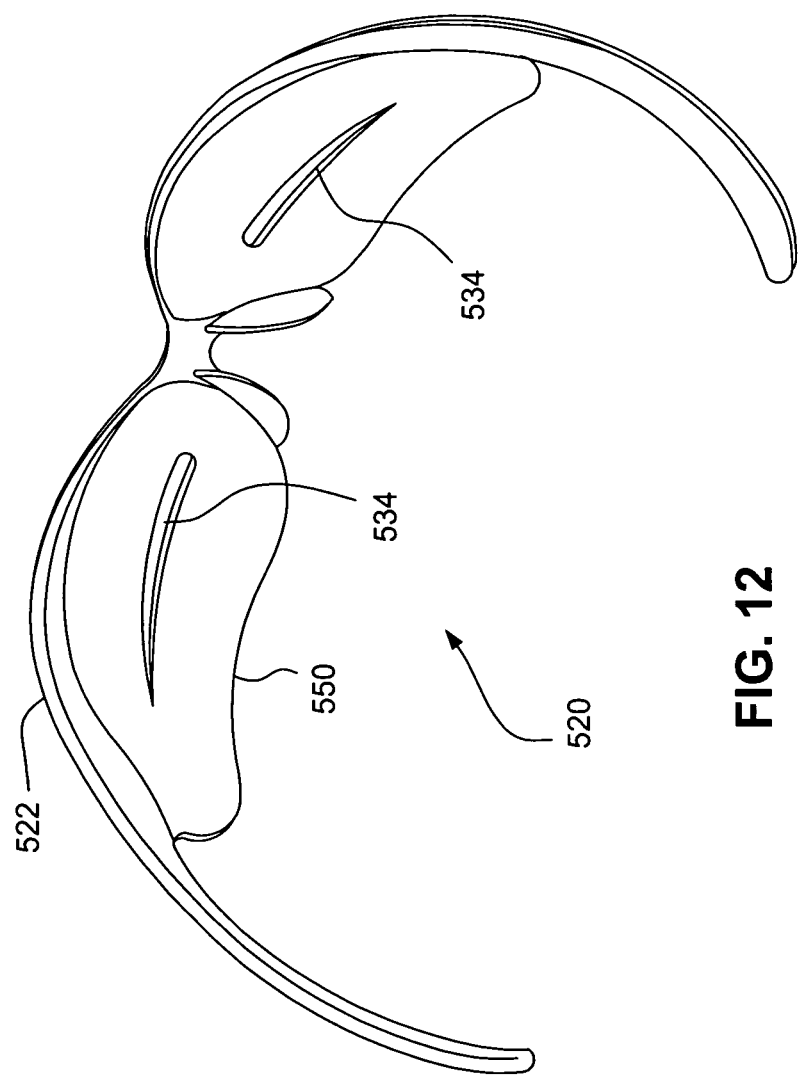
FIG. 12 is a rear perspective view of the embodiment of FIG. 11.

Referring to FIG. 12, shown is a rear view of the protective eyewear 520 of FIG. 11. An optional sealing gasket can be placed around the edge of the lens 550, to prevent airborne particles from contacting the user's eyes when wearing the eyewear 520.

Figure 13:
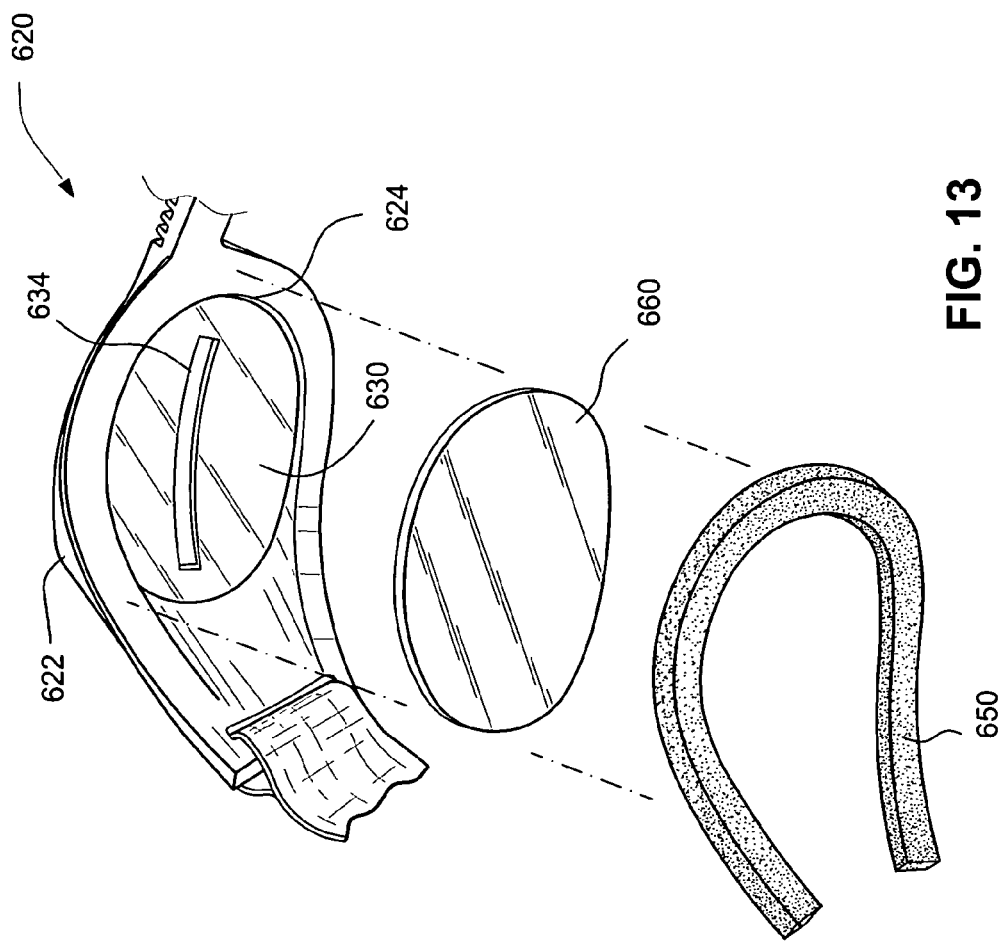
FIG. 13 is an exploded view from the rear of still another embodiment of the present invention with two lens apertures that does not have air inlets or an air supply, with rectangular slits and an optional inner lens.

Referring to FIG. 13, shown is an exploded rear view of still another embodiment comprising eyewear 620 having a frame 622 configured to wear over a user's eyes that has a pair of lens apertures 624. As can be seen, the preferably removable outer lens 630 having rectangular slit 634 is retained in the lens aperture 624 and an optional sealing gasket 650 forms a stagnantly sealed interior space between the lens 630 and the user's face. An optional inner lens 660 also can be provided. Preferably the inner lens is transparent in at least the portions between the user's eyes and the slits 634.

Figure 14:
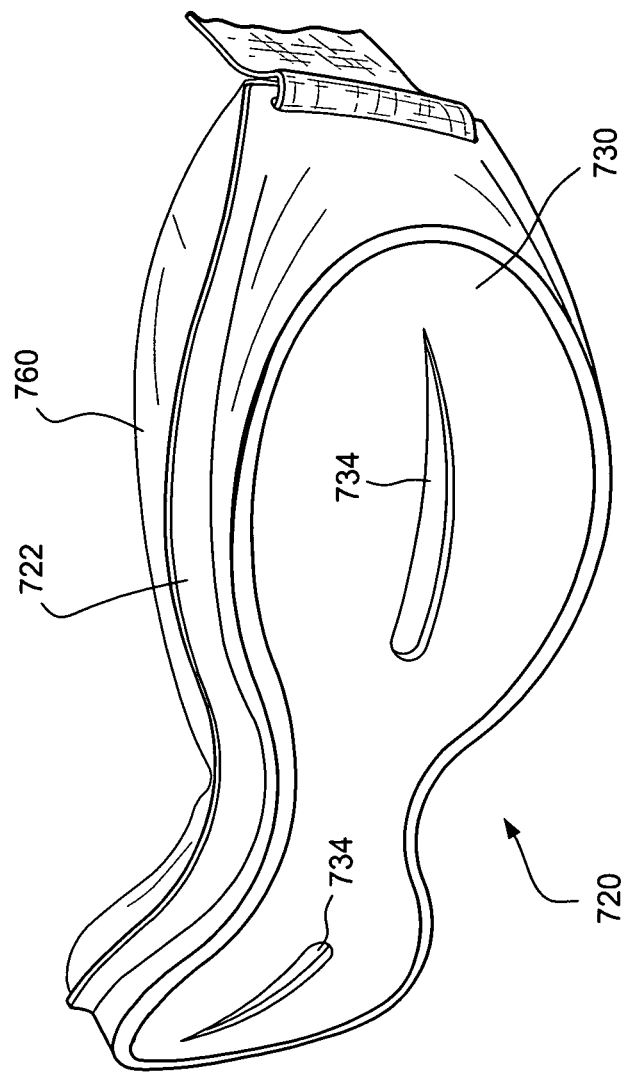
FIG. 14 is a front perspective view of still another alternate embodiment of the present invention with a single lens aperture, but that does not have air inlets or a compressed air supply.

Referring to FIG. 14, shown is still another alternative embodiment comprising eyewear 720 having a frame 722 configured to wear over a user's eyes, that has an integrally formed single lens 730 having slits 734 placed in front of the user's eyes. This embodiment is shaped to stagnantly sealingly conform to the user's face by construction of the frame 722 from a flexible material, optionally with flexible flaps 760 that extend from the frame 722, as is conventional in connection with swim masks. However, any manner of shaping the frame 722 to stagnantly sealingly conform to the user's face is considered to be shaping the eyewear to conform to the user's face. The flaps 760 could include a brow flap, as shown, or temple flaps or cheek flaps. Optionally, the brow flap can be a separable member that is detachably attachable to the frame to block overspray from falling into the user's eyes from above.

Figure 15:
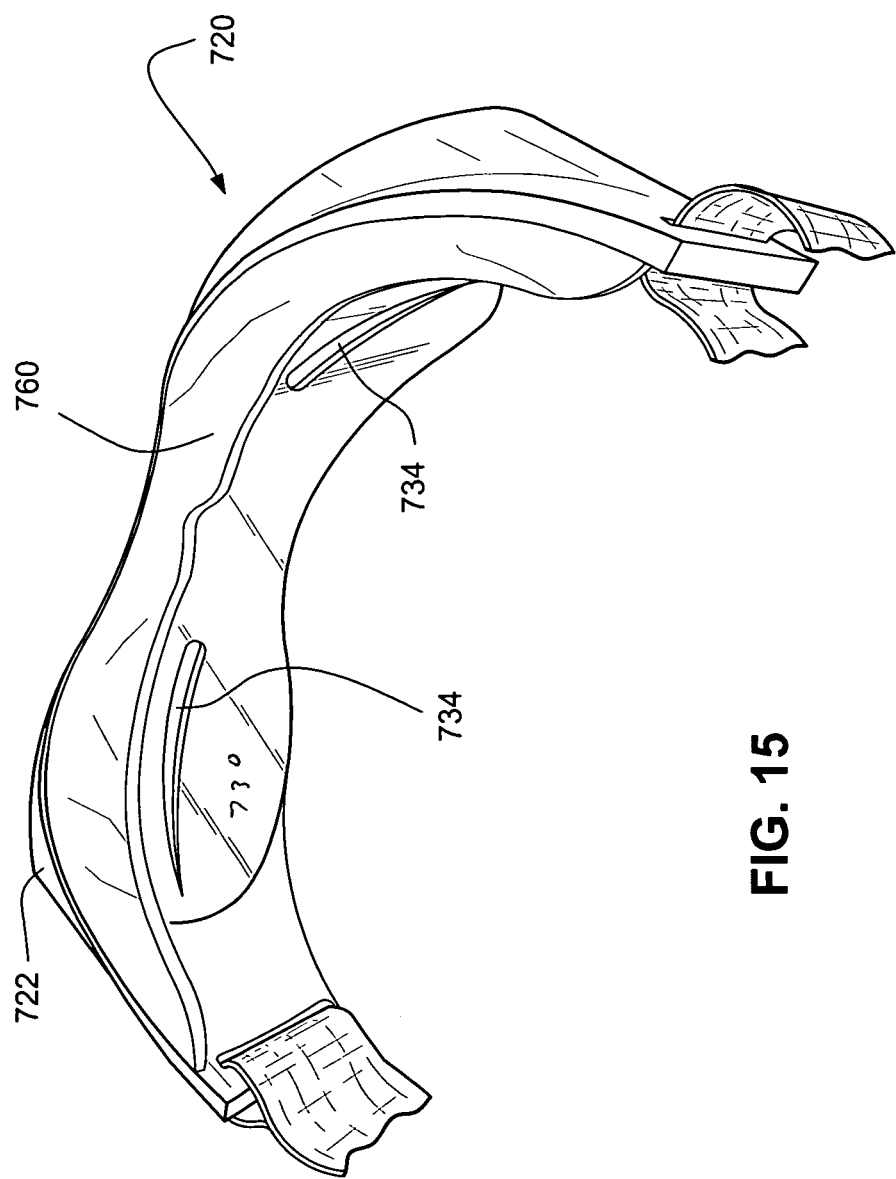
FIG. 15 is a rear perspective view of the embodiment of FIG. 14.

Referring to FIG. 15, shown is a rear view of the protective eyewear 720 of FIG. 14. The flaps 760 extending outwardly from the frame 722 stagnantly sealingly conform to the user's face to create a stagnantly sealed interior space between the integrally formed lens 730 and frame 722 and the user's face. This interior space resists entry of airborne particles through the slits 734 because this space is filled with stagnant "dead air", which may even be expanded by the user's body heat. Further, any airborne particles entering the dead air would not necessarily contact the user's eyes: they may settle on the interior surface of the eyewear 720, on the user's face (other than the eyes), and may even be moved away from the user's eyes by expansion of the dead air by the user's body heat or the air currents caused by blinking of the user's eyelid and eyelashes. Even if some airborne particles still contact the user's eyes, the number of such particles contacting the eyes would be greatly reduced.

Referring to FIGS. 16 to 20, shown is a possible ornamental design for an alternative stylistic embodiment of the present invention.

Figure 16:
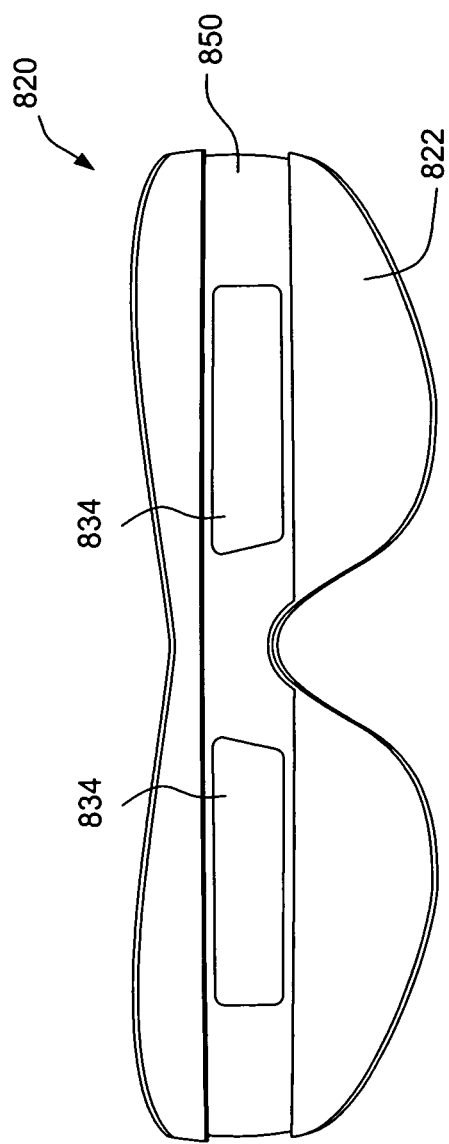
FIG. 16 is a front elevational view of an ornamental embodiment of the present invention.

Referring to FIG. 16, shown is a front view of still another alternative embodiment comprising eyewear 820 having a frame 822 configured to wear over a user's eyes, with two slits 834 for the user's eyes.

Preferably a recessed decorative stripe 850 is formed in the frame 822, and notches 880 (see FIG. 18) to receive the end knobs 870 (see FIG. 17) are formed in the recessed decorative stripe 850.

Figure 17:
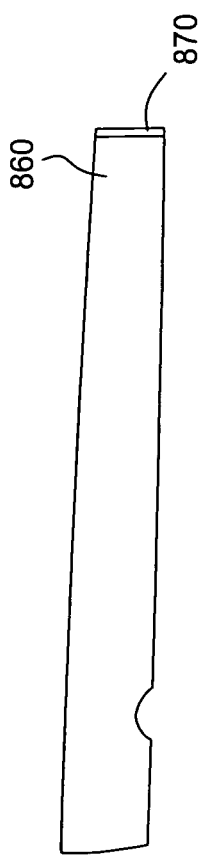
FIG. 17 is a side elevational view diagonally from the front left of an optional sunglass snap-in portion to be received in the embodiment of FIG. 16.

Referring to FIG. 17, shown is a perspective view of an optional arcuate sunglass portion 860 that preferably stagnantly sealingly conforms to the front portion of the recessed decorative stripe 850 in the frame 822 between the notches 880, preferably having end knobs 870 that project inwardly and (as shown in FIG. 18) are received by the notches 880 in the recessed decorative stripe 850 in the frame 822 (see FIG. 18) in order to retain the arcuate sunglass portion 860 on the frame 822.

Referring to FIG. 18, shown is a top plan view of the eyewear 820 of FIG. 16 with the arcuate sunglass portion 860 retained on the frame 822 by snapping the end knobs 870 into the notches 880 in the recessed decorative stripe 850.

Referring to FIG. 19, shown is a side elevational view of the combined eyewear 820 and arcuate sunglass portion 860 of FIG. 18, showing a slit 834 for the user's eyes, and the recessed decorative stripe 850, with the notches 880 formed therein to receive the end knobs 870 and thereby retain the arcuate sunglass portion 860 in place over the slits 834 in the frame 822.

Referring to FIG. 20, shown is a side perspective view of the combined eyewear 820 and arcuate sunglass portion 860 of FIG. 18.

Figure 21:
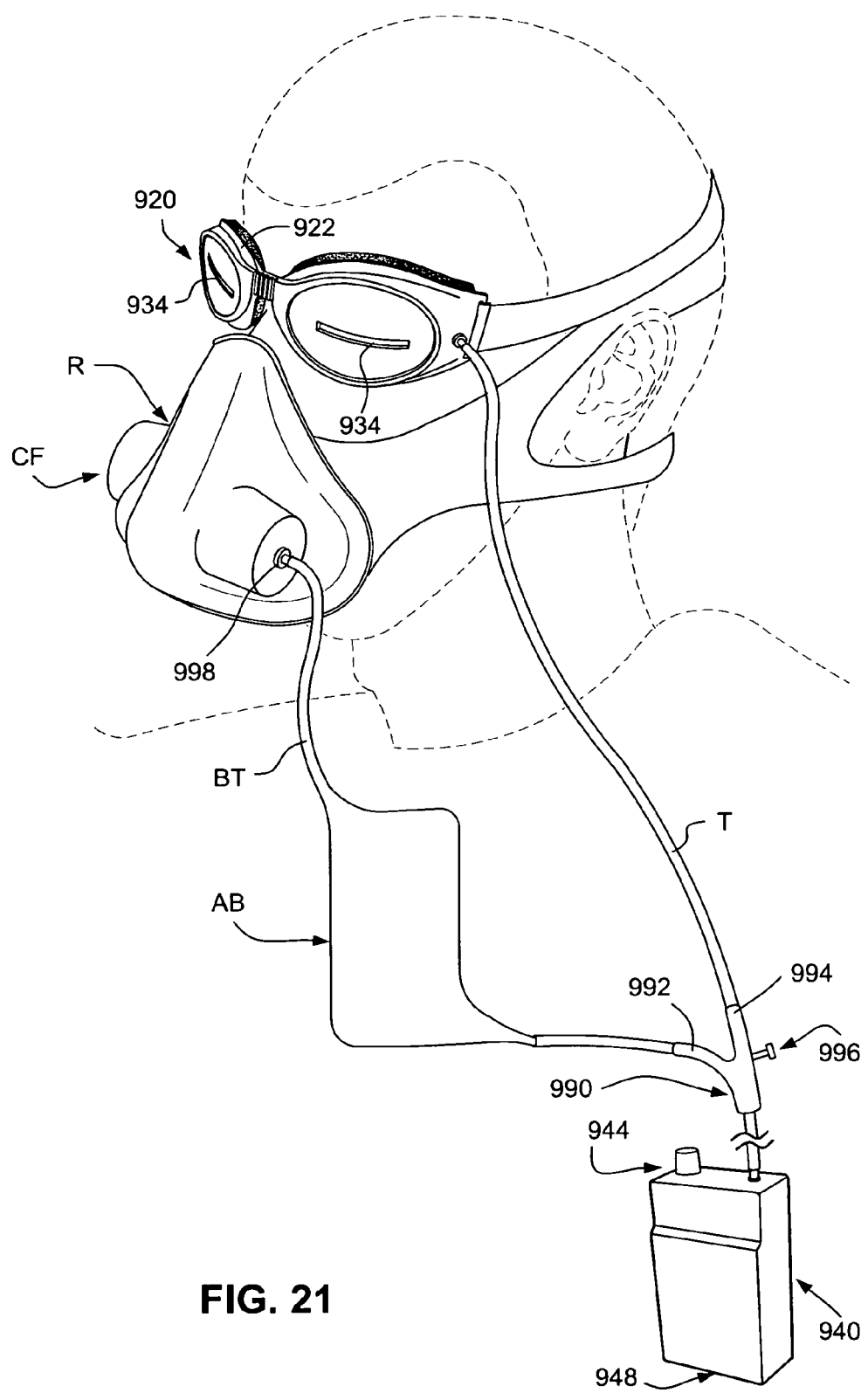
FIG. 21 is a perspective view from the left of another embodiment of the present invention that includes a breathing apparatus.

Referring to FIG. 21, shown is a perspective view from the front of another embodiment of the present invention that includes a breathing apparatus for use in environments with toxic or other undesirable fumes, comprising eyewear 920 having a frame 922 with two slits 934 and an air tube T connecting at a goggles end to an inlet (not shown—see part 26 of FIG. 1) in the frame 922. A compressed air source (here, a portable cordlessly powered pump) 940 is provided having a control knob 944 to control the flow of air. The compressed air source 940 preferably has an air intake with a filter 948, such as an air cartridge filter. Preferably the compressed air source 940 is connected to the air tube T by a "Y" connector 990 having a breathing branch 992 and a goggles branch 994, to which the air tube T is attached. Preferably, an air regulator 996 is provided in the goggles branch 994 to control air flow into the air tube T. Preferably also, a breathing tube BT is attached to the breathing branch 992, and an air bladder AB is optionally provided in the breathing tube BT. As can be seen, the user is wearing a conventional respirator R, which normally has two removable filters, conventionally cartridge filters CF. As can be seen, one of the cartridge filters CF is preferably replaced with a one way valve 998, which closes on exhalation, but opens on inhalation, to which the breathing tube BT is attached. A conventional respirator R resists breathing because air must be drawn through the cartridge filters CF. In this embodiment, the compressed air source can assist breathing by pumping additional air into the respirator R through the breathing branch 990, breathing tube BT and one way valve 998, during inhalation. The optional air bladder AB receives air from the compressed air source 940 while the one way valve 998 is closed during exhalation, and that received air can be inhaled when the one way valve 998 opens during inhalation. In this manner, a compressed air source 940 with lower air flow can be used, because the air bladder can be filled during both inhalation and exhalation, although the user will breathe from the air bladder only during inhalation. Without the air bladder, the compressed air source 940 would need to provide greater air flow to meet the user's inhalation, because the one way valve 998 would be closed and prevent air flow during the user's exhalation. In other words, the bladder provides a reservoir because the compressed air source 940 provides a constant air flow, but a user's breathing is intermittent, alternating between inhalation and exhalation.

As can be seen, air also flows from the compressed air source 940 through the goggles branch 994, air tube T and into the goggles 920, to create an air flow outwardly through the slits 934 that prevents or resists accumulation of paint particles, as explained in connection with the other embodiments described above. The air regulator 996 allows control over the air flowing through the air tube T, separately from the control knob 944 on the compressed air source 940 (which controls air flow through both the breathing tube BT and the air tube T).

Figure 22:
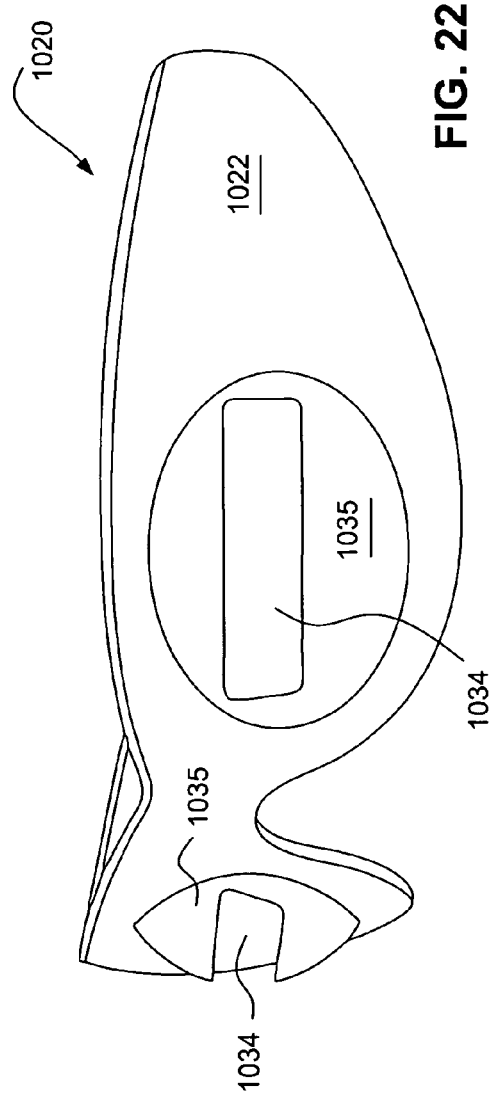
FIG. 22 is a perspective view from the left front of another alternative embodiment having a more extensive frame constituting a mask configured to wear over a user's eyes.

Referring to FIG. 22, shown is a perspective view of still another alternative embodiment comprising eyewear 1020 having a more extensive frame 1022 so as to constitute a mask configured to wear over a user's eyes. Preferably the outer lenses are or have bulges 1035 (preferably, but not necessarily, transparent) that protrude frontwardly, with two slits 1034 formed in the front of the bulges for the user's eyes. The bulges effectively form ledges over the slits. Preferably, the frame 1022 can be made of a flexible material, such as plastic or rubber, that is sufficiently rigid to maintain the slits 1034 and bulges 1035 in place, yet sufficiently flexible to allow the mask to stagnantly sealingly conform to the user's face. The protruding bulges 1035 create deeper pockets of dead air between the slits 1034 and the user's eyes, to prevent or minimize airborne particles that can contact the user's eyes. This embodiment can be retained on the user's face by straps, temple pieces, or other conventional mechanisms (not shown).

Figure 23:
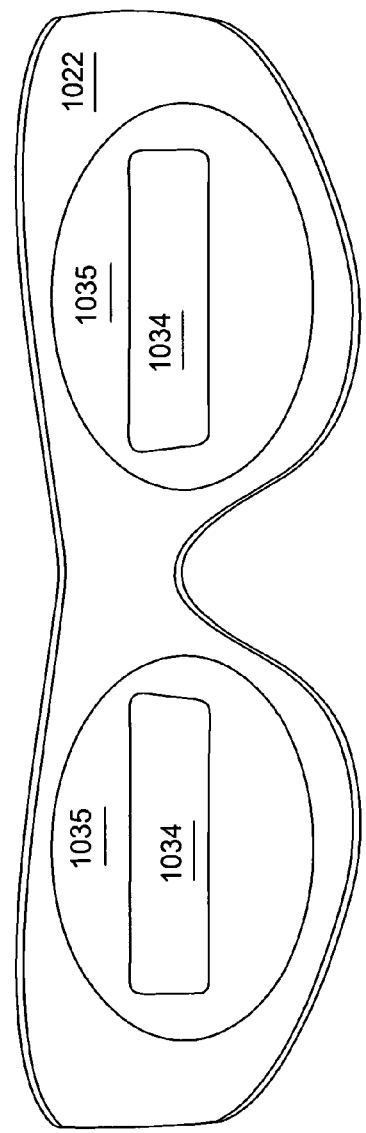
FIG. 23 is a front elevational view of the embodiment of FIG. 22.

FIG. 23 is a front view of the embodiment of FIG. 22.

The embodiments of FIGS. 1 to 10 and 21 are active embodiments, because they require a source of compressed air, so that they can be used where the airborne particles are toxic or otherwise harmful, so that even minimal contact with the user's eyes should be avoided.

The compressed air creates positive pressure to cause air to flow outwardly from the slits. Because there is positive pressure, it is not necessary that the frame and lenses stagnantly sealingly conform (as defined above) to the user's face, but only that the frame conforms to, or is sealed against, the user's face well enough that the compressed air creates a volume of positive pressure in front of the user's eyes, in addition to the air flowing outwardly through the slits (referred to as "positive pressure conforming" or "positive pressure sealed").

The embodiments of FIGS. 11 to 20 and 22-23 are passive embodiments, because no compressed air source is necessary (so that the user can freely move). Instead, the frame stagnantly sealingly conforms to the user's face (either by being shaped to so conform, or having sealing gaskets or outwardly extending flaps that contact the face, or some other sealing structure) and the frame supports, or is integrally formed with, a single simple lens with two slits, or two simple lenses (each with a slit), or a single compound (double) lens with two slits in the outer lens, or two compound (double) lenses, each with a slit in the outer lens, to form a stagnantly sealed interior space in front of the user's eyes (between the frame, lens or lenses, and the user's face (and also in the inter-lens space for compound (double) lenses)). The interior space is deep enough that the partial sealing of the interior space creates a pocket of "dead air" in the interior space, constituting a stagnant air barrier that prevents or reduces the flow of air and airborne particles into the interior space through the slits. Moreover, the user's body heat will tend to heat the air in the interior space, thus expanding the dead air to further prevent or reduce the flow of air and airborne particles through the slits. The airborne particles cannot accumulate on the slits and block the user's vision. Although not all airborne particles may be blocked from entering the interior space, most particles are blocked out of the interior space, and those particles that travel through the slits may land on the user's face or eyelashes, or on the frame or the interior of the lens, rather than the user's eyes. Although some airborne particles may ultimately travel through the slits and contact a user's eyes, the number of particles contacting the user's eyes is greatly reduced, which is almost an infinite improvement over present industry practices, in which painters' eyes are completely unprotected. Although it is recognized that, in conditions of substantial wind, airborne particles may be blown through the slits, users such as spray painters would not work under such windy conditions anyway. Indeed, architects and others specify that spray painting cannot take place if the winds exceed approximately 16 to 32 kilometers per hour (approximately 5 to 10 miles per hour) because the wind then will carry the paint away.

The passive embodiments of FIGS. 16 to 20 and 22-23 are the simplest embodiments, preferably for use when spraying nontoxic paints. Because the paints are nontoxic, it is not necessary to completely prevent airborne paint particles from contacting the user's eyes (although it is desirable to prevent a substantial proportion from doing so), while still reducing the need to stop work to remove and clean eyewear. Thus, this embodiment reduces the amount of paint particles contacting the user's eyes by reducing the exposure of the user's eyes, because the frame is interposed between the paint particles and the user's eyes, so that airborne paint particles can only contact the user's eyes by traveling around the periphery of the frame, or through the slits, without first contacting the user's face or the frame. Further, the user's eyelashes will create air currents that will tend to cause air to flow and carry airborne paint particles away from the user's eyes when the user blinks. In this manner, substantial, though not complete, protection of the user's eyes from nontoxic airborne paint particles is provided, thus reducing the need to stop work to remove and clean eyewear.

The embodiment of FIGS. 16 to 20 has a decorative stripe that is recessed along a front portion, to be stylish and decorative, so that users are not self-conscious about wearing that embodiment. An optional snap-in sunglass portion 860 is provided to fit in the recessed front portion of the stripe, so that the eyewear 820 can also be used when the user is not spray painting. The sunglass portion preferably would not be used when the user is spray painting, because airborne particles would adhere to it.

It may be preferred to modify the embodiments of FIGS. 11 to 20 to make the lenses or the slits extend outwardly. The lenses could extend outwardly by making the lenses bulge outwardly in some manner, such as hemispherically or cylindrically (with the user looking outwardly through the interior portions of the hemispheres or rear ends of the cylinders), so as to increase the distance from the slits to the user's eyes and thereby create a deeper stagnant air barrier (pocket of "dead air") that must be traversed before a paint particle can contact the user's eyes, as shown, for example, in the embodiment of FIGS. 22 and 23. Alternatively, the slits could extend outwardly by providing hollow tubes over the slits that extend outwardly, so that the user can see through the hollow tubes. The cross section of the exterior of the tubes could have any desired shape, and the cross section of the hollow interior could have the same or any other shape, although preferably substantially conforming to the shape of the slits. Outwardly extending tubes would also narrow the range of angles from which overspray could traverse the dead air and contact the user's eyes.

It may also be preferred to modify any of the embodiments to add an outwardly extending brow or lip above the slits to reduce intrusion of airborne particles falling through the slits when the user looks upwards, such as when spray painting a ceiling.

The active embodiment of FIG. 21 allows the present invention to be used in environments with toxic or other undesirable fumes, or where it is otherwise desired to use a respirator to avoid breathing in fumes. Further, with the embodiment of FIG. 21, the invention can be practiced by users with existing respirators, who need only purchase the eyewear 920, air tube T, "Y" fitting 990 with air regulator 996, one way valve 998, breathing tube BT with air bladder AB, and compressed air source 940, which can all be sold together as an accessory kit.

The passive embodiment of FIGS. 22 and 23 covers more of a user's face and may make it more difficult for airborne particles to contact the user's eyes.

In all the embodiments described above, the slit will necessarily restrict the user's field of view in the vertical direction ("vertical field of view"). It would be expected to make the slits the smallest size possible to allow the user to see the area being painted, so as to minimize the amount of paint particles that can intrude through the slits. However, this is not preferred. In addition to seeing the area being painted, the user must be able to see enough of the environment to avoid being injured by objects and other materials in the environment when moving during spray painting. Spray painting is inherently used for painting large areas, so that spray painters must move while painting. Accordingly, spray painters must be able to see enough while wearing the present invention to be able to safely see their environment when moving while spray painting. A vertical field of view of between approximately 90 degrees and approximately 10 degrees is practical; a vertical field of view of approximately 60 degrees and approximately 20 degrees is preferred; and a vertical field of view of approximately 45 to 30 degrees is optimal.

Also, in the active embodiments described above, the slits have a maximum height within a practical range of between approximately 31 millimeters ("mm") (1¼ inch) and approximately 3 mm (⅛ inch); a preferred range of between approximately 19 mm (¾ inch) and approximately 3 mm (⅛ inch); and an optimal range of between approximately 13 mm (½ inch) and approximately 6 mm (¼ inch), and the distance from the cornea of the eye to the slit is within a practical range of between approximately 76 mm (3 inches) to 6 mm (¼ inch); a preferred range of between approximately 38 mm (1½ inch) to 6 mm (¼ inch); and an optimal range of between approximately 16 mm (⅝ inch) and 6 mm (¼ inch). It would be well within the skill of the ordinary artisan to select combinations of these slit heights and distances from the cornea to the slit, and other combinations, to achieve any desired vertical fields of view.

All the embodiments disclosed above solve the long standing problem of lost time and efficiency due to the need to stop painting in order to clean protective eyewear, or to risk injury by foregoing protective eyewear. It would be preferable for the lenses and, optionally, the frames to be transparent (including tinted) so that the user can continue painting even after the lenses have become partially or completely obscured by paint or other airborne particles, because the user can still see through the slits. In this manner, the user can decide whether and when to stop painting in order to clean the lenses because a greater field of vision is desired than provided through the slits. It is also preferred that all the lenses are removable and replaceable, so that, for example, lenses having different shapes and sizes of slits, or different tinting, or new lenses free from scratches, smudges and old paint, can be used. The term "frame" is not restricted to frames that completely encircle the lenses, but also includes frames to which the lenses are attached only at portions (such as the top). Of course, the lenses can be integrally formed with the frames to provide frameless eyewear, which would be equivalent to eyewear with lens apertures and lenses retained in those lens apertures. Integrally formed also includes where the lenses are held in place by having a nosepiece between the lenses (for a two lens embodiment), and temple pieces attached to opposite sides of the lens or lenses, all of which are directly connected to the lens or lenses, so that the eyewear is frameless.

Of course, all the embodiments can be used in combination with other structural features of conventional eyewear, such as adjustable width nosepieces and alternative methods for retaining lenses in frames (magnetically, for example), or retaining eyewear on a user's face (straps, for example).

The present invention provides a practical solution to the problem of meeting workplace safety regulations relating to eye protection for workers who spray paint.

While the present invention has been disclosed in connection with the presently preferred embodiments described herein, it should be understood that there may be other embodiments which fall within the spirit and scope of the invention as defined by the claims. For example, the embodiments of this invention with both inner and outer lenses can be practiced with inner lenses that are fully transparent, or are only transparent in the portions between the user's eyes and the slit. Accordingly, no limitations are to be implied or inferred in this invention except as specifically and explicitly set forth in the claims.

INDUSTRIAL APPLICABILITY

This invention can be used wherever it is desired to provide protective and/or fashionable eyewear for a user of spray painting equipment, or wherever protection against airborne particles is desired while maintaining visibility.

What is claimed is:

1. A device having a frame configured to wear over a user's eyes, and an outer lens retained in said frame having a slit for said user's eyes through which said user can see, the improvement comprising:
    said frame is configured to place said slit in front of said user's eyes, and said frame and said lens are integrally formed of a flexible material;
    further comprising sealing gaskets attached to said frame that contact said user's face;
    whereby said frame and sealing gaskets are configured to stagnantly sealingly conform to said user's face, and to passively create a stagnantly sealed interior space in front of said user's eyes;
    whereby dead air in said interior space becomes a passive stagnant air barrier that creates air resistance against airborne particles from entering through said slit, traversing said interior space and contacting said user's eyes; and
    wherein said user can see through said slit even if said airborne particles are deposited on said outer lens.

2. A device having a frame configured to wear over a user's eyes, and an outer lens retained in said frame having a slit for said user's eyes through which said user can see, the improvement comprising:
    said frame is configured to place said slit in front of said user's eyes, and said frame and said lens are integrally formed of a flexible material;
    further comprising sealing gaskets attached to said frame that contact said user's face;
    whereby said frame and sealing gaskets are configured to stagnantly sealingly conform to said user's face, and to create a stagnantly sealed interior space in front of said user's eyes;
    whereby dead air in said interior space becomes a stagnant air barrier that creates air resistance against airborne particles from entering through said slit, traversing said interior space and contacting said user's eyes; and
    wherein said user can see through said slit even if said airborne particles are deposited on said outer lens;
    a protective inner lens that is transparent at least in portions between said user's eyes and said slit, retained in said frame behind said outer lens, whereby said user can see through said transparent portions of said inner lens and through said slit.

3. A device according to claim 1,
    wherein said outer lens having a slit comprises two outer lenses, each outer lens having a slit for one of said user's eyes.

4. A device, according to claim 2, wherein said outer lens having a slit comprises two outer lenses, each outer lens having a slit for one of said user's eyes; and
    wherein said protective inner lens comprises two protective inner lenses retained in said frame, each behind a corresponding one of said outer lenses.

5. A device according to any one of claims 1 to 4, wherein said frame is configured to stagnantly sealingly conform to said user's face by a removably detachable brow flap.

6. A device, comprising:
    a frame configured to wear over a user's eyes, and to stagnantly sealingly conform to said user's face; and
    a lens having a slit for said user's eyes mounted in said frame in front of said user's eyes;
    wherein said frame and said lens are integrally formed of a flexible material;
    further comprising sealing gaskets attached to said frame that contact said user's face to passively create a stagnantly sealed interior space in front of said user's eyes;
    whereby dead air in said interior space becomes a passive stagnant air barrier that creates air resistance against airborne particles from entering through said slit, traversing said interior space and contacting said user's eyes; and
    wherein said user can see through said slit even if said airborne particles are deposited on said lens.

7. A device, according to claim 6,
    wherein said lens having a slit comprises two outer lenses, each outer lens having a slit for one of said user's eyes.

8. A process for using eyewear having a lens with a slit, wherein said eyewear has a frame configured to place said slit in front of said user's eyes, and said frame and said lens are integrally formed of a flexible material, with sealing gaskets attached to said frame that contact said user's face to stagnantly sealingly conform to said user's face, comprising:

providing said eyewear to a user to wear when performing spray painting with nontoxic paint to passively create a stagnantly sealed interior space in front of said user's eyes;

whereby dead air in said interior space becomes a passive stagnant air barrier that creates air resistance against nontoxic airborne paint particles from entering through said slit, traversing said interior space and contacting said user's eyes;

whereby substantial amounts of said nontoxic airborne paint particles contact said lens and said user's face, thereby substantially reducing amounts of said nontoxic airborne particles contacting said user's eyes; and wherein said user can see through said slit even if said nontoxic airborne particles are deposited on said lens thereby reducing the need to stop work to remove said nontoxic paint particles that obscure vision.

9. A device according to claim 1, wherein said outer lens bulges frontwardly and said slit is formed in the front of said bulge.

10. A device according to any one of claims 1 to 6, 8, and 9, further comprising outwardly extending flaps attached to said frame that contact said user's face, whereby said frame is configured to sealingly conform to said user's face.

11. A device, comprising:

a frame configured to wear over a user's eyes;

an outer lens retained in said frame having a slit for said user's eyes through which said user can see, wherein said frame is configured to place said slit in front of said user's eyes, and said frame and said lens are integrally formed of a flexible material sufficiently rigid to maintain said slits in place, yet sufficiently flexible to stagnantly sealingly conform to said user's face, whereby said frame passively creates a stagnantly sealed interior space in front of said user's eyes;

whereby dead air in said interior space becomes a passive stagnant air barrier that creates air resistance against airborne particles entering through said slit, traversing said interior space and contacting said user's eyes; and wherein said user can see through said slit even if said airborne particles are deposited on said outer lens.

12. A device according to claim 11, wherein said outer lens having a slit comprises two outer lenses, each outer lens having a slit for one of said user's eyes.

* * * * *